United States Patent [19]
Potter et al.

[11] Patent Number: 5,985,289
[45] Date of Patent: *Nov. 16, 1999

[54] HAEMOPHILUS SOMNUS OUTER MEMBRANE PROTEIN EXTRACT ENRICHED WITH IRON-REGULATED PROTEINS

[75] Inventors: Andrew A. Potter; Richard J. Harland, both of Saskatoon, Canada

[73] Assignee: University of Saskatchewan, Saskatoon, Canada

[*] Notice: This patent is subject to a terminal disclaimer.

[21] Appl. No.: 08/535,837

[22] Filed: Sep. 28, 1995

Related U.S. Application Data

[63] Continuation of application No. 07/908,253, Jul. 2, 1992, Pat. No. 5,534,256.

[51] Int. Cl.$^6$ .................................................. A61K 39/102
[52] U.S. Cl. ..................... 424/256.1; 424/184.1; 424/193.1; 424/203.1; 424/236.1; 424/255.1; 424/278.1; 424/282.1
[58] Field of Search ............... 424/256.1, 184.1, 424/255.1, 193.1, 203.1, 236.1, 278.1, 282.1

[56] References Cited

U.S. PATENT DOCUMENTS

| | | | |
|---|---|---|---|
| 4,346,074 | 8/1982 | Gilmour et al. | 424/42 |
| 4,877,613 | 10/1989 | Vedros et al. | 424/92 |
| 4,957,739 | 9/1990 | Berget et al. | 424/92 |
| 4,981,685 | 1/1991 | Healey | 424/92 |
| 5,055,400 | 10/1991 | Lo et al. | 435/69.1 |
| 5,141,743 | 8/1992 | Schryvers | 424/92 |
| 5,292,869 | 3/1994 | Schryvers | 530/413 |

FOREIGN PATENT DOCUMENTS

WO 91/15237  10/1991  WIPO ............................ A61K 54/02

OTHER PUBLICATIONS

Yu et al Infection and Immunity 60:2992–2994, 1992.
O Gunnarino et al Microbial Pathogenesis 9:397–406, 1990.
Pidcock et al—1988 Infect. Immun. 56(4):721–725.
Lee et al. 1992 Infect Immun. 60(3): 810–816.
Biostar Brochure, entitled "3 New Vaccines", released on Jul. 6, 1991.
Bolin, C.A., and Jensen, A.E., *Infect. Immun.* (1987) 55:1239–1242.
Conlon et al., *Infect. Immun.* (1991) 59:587–591.
Corbeil, L.B., *Can. J. Vet. Res.* (1990) 54:557–562.
Database excerpt—Animal Pharm. World Animal Health News No. 228.
Donanchie et al., *J. Gen. Micro.* (1984) 130:1209–1216.
Gentry et al., *Vet. Immunology and Immunopathology* (1985) 9:239–250.
Griffiths et al., *Infect. Immun.* (1985) 47:808–813.
Harris et al., *Can J. Vet. Res.* (1990) 30:816–822.
Himmel et al., *Am. J. Vet. Res.* (1982) 43:764–767.
Humphrey et al., *Vet. Bull.* (1983) 53:987–1004.
Lee, B.C., *Infect. Immun.* (1992) 60:810–816.
Lessley et al., *Veterinary Immunology and Immunopathology* (1985) 10:279–296.
Lo et al., *Infect. Immun.* (1985) 50:667–67.
Ogunnariwo et al., *Microbial Pathogenesis* (1990) 9:397–406.
Philbey et al., *Aust. Vet. J.* (1991) 88:387–390.
Shewen, P.E. and Wilkie, B.N., *Am. J. Vet. Res.* (1983) 44:715–719.
Shewen, P.E. and Wilkie, B.N., in *Can. J. Vet. Res.* (1988) 52:30–36.
Silva et al., *Can. J. Vet. Res.* (1990) 54:326–330.
Strathdee, C.A. and Lo, R.Y.C., *Infect. Immun.* (1987) 55:3233–3236.
Stephens et al., *Am. J. Vet. Res.* (1984) 45:234–239.
Yates, W.D.G., *Can. J. Comp. Med.* (1982) 46:225–263.

*Primary Examiner*—James C. Housel
*Assistant Examiner*—Jennifer Graser
*Attorney, Agent, or Firm*—Robins and Associates

[57] ABSTRACT

New subunit vaccines from *Haemophilus somnus* are disclosed. The vaccines include an outer membrane protein extract of *H. somnus* which is enriched with iron-regulated proteins. Additional antigens, such as antigens derived from *Pasteurella haemolytica*, can be included in the vaccine composition to provide protection against a variety of disease states.

8 Claims, 9 Drawing Sheets

```
1    MGTRLTTLSNGLKNTLTATKSGLHKAGQSLTQAGSSLKTGAKKIILYIPQNYQYDTEQGN
61   GLQDLVKAAEELGIEVQREERNNIATAQTSLGTIQTAIGLTERGIVLSAPQIDKLLQKTK
121  AGQALGSAESIVQNANKAKTVLSGIQSILGSVLAGMDLDEALQNNSNQHALAKAGLELTN
181  SLIENIANSVKTLDEFGEQISQFGSKLQNIKGLGTLGDKLKNIGGLDKAGLGLDVISGLL
241  SGATAALVLADKNASTAKKVGAGFELANQVVGNITKAVSSYILAQRVAAGLSSTGPVAAL
301  IASTVSLAISPLAFAGIADKFNHAKSLESYAERFKKLGYDGDNLLAEYQRGTGTIDASVT
361  AINTALAAIAGGVSAAAGRRIRGIPGDPVVLQRRDWENPGVTQLNRLAAHPPFASWRNSE
421  EARTDRPSQQLRSLNGEWRFAWFPAPEAVPESWLECDLPEADTVVVPSNWQMHGYDAPIY
481  TNVTYPITVNPPFVPTENPTGCYSLTFNVDESWLQEGQTRIIFDGVNSAFHLWCNGRWVG
541  YGQDSRLPSEFDLSAFLRAGENRLAVMVLRWSDGSYLEDQDMWRMSGIFRDVSLLHKPTT
601  QISDFHVATRFNDDFSRAVLEAEVQMCGELRDYLRVTVSLWQGETQVASGTAPFGGEIID
661  ERGGYADRVTLRLNVENPKLWSAEIPNLYRAVVELHTADGTLIEAEACDVGFREVRIENG
721  LLLLNGKPLLIRGVNRHEHHPLHGQVMDEQTMVQDILLMKQNNFNAVRCSHYPNHPLWYT
781  LCDRYGLYVVDEANIETHGMVPMNRLTDDPRWLPAMSERVTRMVQRDRNHPSVIIWSLGN
841  ESGHGANHDALYRWIKSVDPSRPVQYEGGGADTTATDIICPMYARVDEDQPFPAVPKWSI
901  KKWLSLPGETRPLILCEYAHAMGNSLGGFAKYWQAFRQYPRLQGGFVWDWVDQSLIKYDE
961  NGNPWSAYGGDFGDTPNDRQFCMNGLVFADRTPHPALTEAKHQQQFFQFRLSGQTIEVTS
1021 EYLFRHSDNELLHWMVALDGKPLASGEVPLDVAPQGKQLIELPELPQPESAGQLWLTVRV
1081 VQPNATAWSEAGHISAWQQWRLAENLSVTLPAASHAIPHLTTSEMDFCIELGNKRWQFNR
1141 QSGFLSQMWIGDKKQLLTPLRDQFTRAPLDNDIGVSEATRIDPNAWVERWKAAGHYQAEA
1201 ALLQCTADTLADAVLITTAHAWQHQGKTLFISRKTYRIDGSGQMAITVDVEVASDTPHPA
1261 RIGLNCQLAQVAERVNWLGLGPQENYPDRLTAACFDRWDLPLSDMYTPYVFPSENGLRCG
1321 TRELNYGPHQWRGDFQFNISRYSQQQLMETSHRHLLHAEEGTWLNIDGFHMGIGGDDSWS
1381 PSVSAEFQLSAGRYHYQLVWCQK
```

FIG.3

```
              10         20         30         40         50         60
     *    *    *    *    *    *    *    *    *    *    *    *
ATG GCT ACT GTT ATA GAT CTA AGC TTC CCA AAA ACT GGG GCA AAA AAA ATT ATC CTC TAT
TAC CGA TGA CAA TAT CTA GAT TCG AAG GGT TTT TGA CCC CGT TTT TTT TAA TAG GAG ATA
Met Ala Thr Val Ile Asp Leu Ser Phe Pro Lys Thr Gly Ala Lys Lys Ile Ile Leu Tyr>
___c___c___c___c___c____RECOMBINANT LEUKOTOXIN PEPTIDE_c___c___c___c___c___c___>
___a___a___VECTOR SEQUENCE_a___a___a__>

70         80         90        100        110        120
     *    *    *    *    *    *    *    *    *    *    *    *
ATT CCC CAA AAT TAC CAA TAT GAT ACT GAA CAA GGT AAT GGT TTA CAG GAT TTA GTC AAA
TAA GGG GTT TTA ATG GTT ATA CTA TGA CTT GTT CCA TTA CCA AAT GTC CTA AAT CAG TTT
Ile Pro Gln Asn Tyr Gln Tyr Asp Thr Glu Gln Gly Asn Gly Leu Gln Asp Leu Val Lys>
___c___c___c___c___c____RECOMBINANT LEUKOTOXIN PEPTIDE_c___c___c___c___c___c___>

130        140        150        160        170        180
     *    *    *    *    *    *    *    *    *    *    *    *
GCG GCC GAA GAG TTG GGG ATT GAG GTA CAA AGA GAA GAA CGC AAT AAT ATT GCA ACA GCT
CGC CGG CTT CTC AAC CCC TAA CTC CAT GTT TCT CTT CTT GCG TTA TTA TAA CGT TGT CGA
Ala Ala Glu Glu Leu Gly Ile Glu Val Gln Arg Glu Glu Arg Asn Asn Ile Ala Thr Ala>
___c___c___c___c___c____RECOMBINANT LEUKOTOXIN PEPTIDE_c___c___c___c___c___c___>

190        200        210        220        230        240
     *    *    *    *    *    *    *    *    *    *    *    *
CAA ACC AGT TTA GGC ACG ATT CAA ACC GCT ATT GGC TTA ACT GAG CGT GGC ATT GTG TTA
GTT TGG TCA AAT CCG TGC TAA GTT TGG CGA TAA CCG AAT TGA CTC GCA CCG TAA CAC AAT
Gln Thr Ser Leu Gly Thr Ile Gln Thr Ala Ile Gly Leu Thr Glu Arg Gly Ile Val Leu>
___c___c___c___c___c____RECOMBINANT LEUKOTOXIN PEPTIDE_c___c___c___c___c___c___>

250        260        270        280        290        300
     *    *    *    *    *    *    *    *    *    *    *    *
TCC GCT CCA CAA ATT GAT AAA TTG CTA CAG AAA ACT AAA GCA GGC CAA GCA TTA GGT TCT
AGG CGA GGT GTT TAA CTA TTT AAC GAT GTC TTT TGA TTT CGT CCG GTT CGT AAT CCA AGA
Ser Ala Pro Gln Ile Asp Lys Leu Leu Gln Lys Thr Lys Ala Gly Gln Ala Leu Gly Ser>
___c___c___c___c___c____RECOMBINANT LEUKOTOXIN PEPTIDE_c___c___c___c___c___c___>

310        320        330        340        350        360
     *    *    *    *    *    *    *    *    *    *    *    *
GCC GAA AGC ATT GTA CAA AAT GCA AAT AAA GCC AAA ACT GTA TTA TCT GGC ATT CAA TCT
CGG CTT TCG TAA CAT GTT TTA CGT TTA TTT CGG TTT TGA CAT AAT AGA CCG TAA GTT AGA
Ala Glu Ser Ile Val Gln Asn Ala Asn Lys Ala Lys Thr Val Leu Ser Gly Ile Gln Ser>
___c___c___c___c___c____RECOMBINANT LEUKOTOXIN PEPTIDE_c___c___c___c___c___c___>

370        380        390        400        410        420
     *    *    *    *    *    *    *    *    *    *    *    *
ATT TTA GGC TCA GTA TTG GCT GGA ATG GAT TTA GAT GAG GCC TTA CAG AAT AAC AGC AAC
TAA AAT CCG AGT CAT AAC CGA CCT TAC CTA AAT CTA CTC CGG AAT GTC TTA TTG TCG TTG
Ile Leu Gly Ser Val Leu Ala Gly Met Asp Leu Asp Glu Ala Leu Gln Asn Asn Ser Asn>
___c___c___c___c___c____RECOMBINANT LEUKOTOXIN PEPTIDE_c___c___c___c___c___c___>

430        440        450        460        470        480
     *    *    *    *    *    *    *    *    *    *    *    *
CAA CAT GCT CTT GCT AAA GCT GGC TTG GAG CTA ACA AAT TCA TTA ATT GAA AAT ATT GCT
GTT GTA CGA GAA CGA TTT CGA CCG AAC CTC GAT TGT TTA AGT AAT TAA CTT TTA TAA CGA
Gln His Ala Leu Ala Lys Ala Gly Leu Glu Leu Thr Asn Ser Leu Ile Glu Asn Ile Ala>
___c___c___c___c___c____RECOMBINANT LEUKOTOXIN PEPTIDE_c___c___c___c___c___c___>
```

FIG.5A

```
          490         500         510         520         530         540
    *      *     *      *     *      *     *      *     *      *     *
AAT TCA GTA AAA ACA CTT GAC GAA TTT GGT GAG CAA ATT AGT CAA TTT GGT TCA AAA CTA
TTA AGT CAT TTT TGT GAA CTG CTT AAA CCA CTC GTT TAA TCA GTT AAA CCA AGT TTT GAT
Asn Ser Val Lys Thr Leu Asp Glu Phe Gly Glu Gln Ile Ser Gln Phe Gly Ser Lys Leu>
___c___c___c___c___c_____RECOMBINANT LEUKOTOXIN PEPTIDE_c____c____c____c____c____c___>

550         560         570         580         590         600
    *      *     *      *     *      *     *      *     *      *     *
CAA AAT ATC AAA GGC TTA GGG ACT TTA GGA GAC AAA CTC AAA AAT ATC GGT GGA CTT GAT
GTT TTA TAG TTT CCG AAT CCC TGA AAT CCT CTG TTT GAG TTT TTA TAG CCA CCT GAA CTA
Gln Asn Ile Lys Gly Leu Gly Thr Leu Gly Asp Lys Leu Lys Asn Ile Gly Gly Leu Asp>
___c___c___c___c___c_____RECOMBINANT LEUKOTOXIN PEPTIDE_c____c____c____c____c____c___>

610         620         630         640         650         660
    *      *     *      *     *      *     *      *     *      *     *
AAA GCT GGC CTT GGT TTA GAT GTT ATC TCA GGG CTA TTA TCG GGC GCA ACA GCT GCA CTT
TTT CGA CCG GAA CCA AAT CTA CAA TAG AGT CCC GAT AAT AGC CCG CGT TGT CGA CGT GAA
Lys Ala Gly Leu Gly Leu Asp Val Ile Ser Gly Leu Leu Ser Gly Ala Thr Ala Ala Leu>
___c___c___c___c___c_____RECOMBINANT LEUKOTOXIN PEPTIDE_c____c____c____c____c____c___>

670         680         690         700         710         720
    *      *     *      *     *      *     *      *     *      *     *
GTA CTT GCA GAT AAA AAT GCT TCA ACA GCT AAA AAA GTG GGT GCG GGT TTT GAA TTG GCA
CAT GAA CGT CTA TTT TTA CGA AGT TGT CGA TTT TTT CAC CCA CGC CCA AAA CTT AAC CGT
Val Leu Ala Asp Lys Asn Ala Ser Thr Ala Lys Lys Val Gly Ala Gly Phe Glu Leu Ala>
___c___c___c___c___c_____RECOMBINANT LEUKOTOXIN PEPTIDE_c____c____c____c____c____c___>

730         740         750         760         770         780
    *      *     *      *     *      *     *      *     *      *     *
AAC CAA GTT GTT GGT AAT ATT ACC AAA GCC GTT TCT TCT TAC ATT TTA GCC CAA CGT GTT
TTG GTT CAA CAA CCA TTA TAA TGG TTT CGG CAA AGA AGA ATG TAA AAT CGG GTT GCA CAA
Asn Gln Val Val Gly Asn Ile Thr Lys Ala Val Ser Ser Tyr Ile Leu Ala Gln Arg Val>
___c___c___c___c___c_____RECOMBINANT LEUKOTOXIN PEPTIDE_c____c____c____c____c____c___>

790         800         810         820         830         840
    *      *     *      *     *      *     *      *     *      *     *
GCA GCA GGT TTA TCT TCA ACT GGG CCT GTG GCT GCT TTA ATT GCT TCT ACT GTT TCT CTT
CGT CGT CCA AAT AGA AGT TGA CCC GGA CAC CGA CGA AAT TAA CGA AGA TGA CAA AGA GAA
Ala Ala Gly Leu Ser Ser Thr Gly Pro Val Ala Ala Leu Ile Ala Ser Thr Val Ser Leu>
___c___c___c___c___c_____RECOMBINANT LEUKOTOXIN PEPTIDE_c____c____c____c____c____c___>

850         860         870         880         890         900
    *      *     *      *     *      *     *      *     *      *     *
GCG ATT AGC CCA TTA GCA TTT GCC GGT ATT GCC GAT AAA TTT AAT CAT GCA AAA AGT TTA
CGC TAA TCG GGT AAT CGT AAA CGG CCA TAA CGG CTA TTT AAA TTA GTA CGT TTT TCA AAT
Ala Ile Ser Pro Leu Ala Phe Ala Gly Ile Ala Asp Lys Phe Asn His Ala Lys Ser Leu>
___c___c___c___c___c_____RECOMBINANT LEUKOTOXIN PEPTIDE_c____c____c____c____c____c___>

910         920         930         940         950         960
    *      *     *      *     *      *     *      *     *      *     *
GAG AGT TAT GCC GAA CGC TTT AAA AAA TTA GGC TAT GAC GGA GAT AAT TTA TTA GCA GAA
CTC TCA ATA CGG CTT GCG AAA TTT TTT AAT CCG ATA CTG CCT CTA TTA AAT AAT CGT CTT
Glu Ser Tyr Ala Glu Arg Phe Lys Lys Leu Gly Tyr Asp Gly Asp Asn Leu Leu Ala Glu>
___c___c___c___c___c_____RECOMBINANT LEUKOTOXIN PEPTIDE_c____c____c____c____c____c___>
```

FIG.5B

```
              970         980         990        1000        1010        1020
          *    *     *    *     *    *     *    *     *    *     *    *
    TAT CAG CGG GGA ACA GGG ACT ATT GAT GCA TCG GTT ACT GCA ATT AAT ACC GCA TTG GCC
    ATA GTC GCC CCT TGT CCC TGA TAA CTA CGT AGC CAA TGA CGT TAA TTA TGG CGT AAC CGG
    Tyr Gln Arg Gly Thr Gly Thr Ile Asp Ala Ser Val Thr Ala Ile Asn Thr Ala Leu Ala>
    ___c___c___c___c___c____RECOMBINANT LEUKOTOXIN PEPTIDE_c___c___c___c___c___c___>

1030        1040        1050        1060        1070        1080
          *    *     *    *     *    *     *    *     *    *     *    *
    GCT ATT GCT GGT GGT GTG TCT GCT GCT GCA GCC GGC TCG GTT ATT GCT TCA CCG ATT GCC
    CGA TAA CGA CCA CCA CAC AGA CGA CGA CGT CGG CCG AGC CAA TAA CGA AGT GGC TAA CGG
    Ala Ile Ala Gly Gly Val Ser Ala Ala Ala Ala Gly Ser Val Ile Ala Ser Pro Ile Ala>
    ___c___c___c___c___c____RECOMBINANT LEUKOTOXIN PEPTIDE_c___c___c___c___c___c___>

1090        1100        1110        1120        1130        1140
          *    *     *    *     *    *     *    *     *    *     *    *
    TTA TTA GTA TCT GGG ATT ACC GGT GTA ATT TCT ACG ATT CTG CAA TAT TCT AAA CAA GCA
    AAT AAT CAT AGA CCC TAA TGG CCA CAT TAA AGA TGC TAA GAC GTT ATA AGA TTT GTT CGT
    Leu Leu Val Ser Gly Ile Thr Gly Val Ile Ser Thr Ile Leu Gln Tyr Ser Lys Gln Ala>
    ___c___c___c___c___c____RECOMBINANT LEUKOTOXIN PEPTIDE_c___c___c___c___c___c___>

1150        1160        1170        1180        1190        1200
          *    *     *    *     *    *     *    *     *    *     *    *
    ATG TTT GAG CAC GTT GCA AAT AAA ATT CAT AAC AAA ATT GTA GAA TGG GAA AAA AAT AAT
    TAC AAA CTC GTG CAA CGT TTA TTT TAA GTA TTG TTT TAA CAT CTT ACC CTT TTT TTA TTA
    Met Phe Glu His Val Ala Asn Lys Ile His Asn Lys Ile Val Glu Trp Glu Lys Asn Asn>
    ___c___c___c___c___c____RECOMBINANT LEUKOTOXIN PEPTIDE_c___c___c___c___c___c___>

1210        1220        1230        1240        1250        1260
          *    *     *    *     *    *     *    *     *    *     *    *
    CAC GGT AAG AAC TAC TTT GAA AAT GGT TAC GAT GCC CGT TAT CTT GCG AAT TTA CAA GAT
    GTG CCA TTC TTG ATG AAA CTT TTA CCA ATG CTA CGG GCA ATA GAA CGC TTA AAT GTT CTA
    His Gly Lys Asn Tyr Phe Glu Asn Gly Tyr Asp Ala Arg Tyr Leu Ala Asn Leu Gln Asp>
    ___c___c___c___c___c____RECOMBINANT LEUKOTOXIN PEPTIDE_c___c___c___c___c___c___>

1270        1280        1290        1300        1310        1320
          *    *     *    *     *    *     *    *     *    *     *    *
    AAT ATG AAA TTC TTA CTG AAC TTA AAC AAA GAG TTA CAG GCA GAA CGT GTC ATC GCT ATT
    TTA TAC TTT AAG AAT GAC TTG AAT TTG TTT CTC AAT GTC CGT CTT GCA CAG TAG CGA TAA
    Asn Met Lys Phe Leu Leu Asn Leu Asn Lys Glu Leu Gln Ala Glu Arg Val Ile Ala Ile>
    ___c___c___c___c___c____RECOMBINANT LEUKOTOXIN PEPTIDE_c___c___c___c___c___c___>

1330        1340        1350        1360        1370        1380
          *    *     *    *     *    *     *    *     *    *     *    *
    ACT CAG CAG CAA TGG GAT AAC AAC ATT GGT GAT TTA GCT GGT ATT AGC CGT TTA GGT GAA
    TGA GTC GTC GTT ACC CTA TTG TTG TAA CCA CTA AAT CGA CCA TAA TCG GCA AAT CCA CTT
    Thr Gln Gln Gln Trp Asp Asn Asn Ile Gly Asp Leu Ala Gly Ile Ser Arg Leu Gly Glu>
    ___c___c___c___c___c____RECOMBINANT LEUKOTOXIN PEPTIDE_c___c___c___c___c___c___>

1390        1400        1410        1420        1430        1440
          *    *     *    *     *    *     *    *     *    *     *    *
    AAA GTC CTT AGT GGT AAA GCC TAT GTG GAT GCG TTT GAA GAA GGC AAA CAC ATT AAA GCC
    TTT CAG GAA TCA CCA TTT CGG ATA CAC CTA CGC AAA CTT CTT CCG TTT GTG TAA TTT CGG
    Lys Val Leu Ser Gly Lys Ala Tyr Val Asp Ala Phe Glu Glu Gly Lys His Ile Lys Ala>
    ___c___c___c___c___c____RECOMBINANT LEUKOTOXIN PEPTIDE_c___c___c___c___c___c___>
```

FIG.5C

```
              1450          1460          1470          1480          1490          1500
       .       *      .      *      .      *      .      *      .      *      .      *
GAT AAA TTA GTA CAG TTG GAT TCG GCA AAC GGT ATT ATT GAT GTG AGT AAT TCG GGT AAA
CTA TTT AAT CAT GTC AAC CTA AGC CGT TTG CCA TAA TAA CTA CAC TCA TTA AGC CCA TTT
Asp Lys Leu Val Gln Leu Asp Ser Ala Asn Gly Ile Ile Asp Val Ser Asn Ser Gly Lys>

1510          1520          1530          1540          1550          1560
       .       *      .      *      .      *      .      *      .      *      .      *
GCG AAA ACT CAG CAT ATC TTA TTC AGA ACG CCA TTA TTG ACG CCG GGA ACA GAG CAT CGT
CGC TTT TGA GTC GTA TAG AAT AAG TCT TGC GGT AAT AAC TGC GGC CCT TGT CTC GTA GCA
Ala Lys Thr Gln His Ile Leu Phe Arg Thr Pro Leu Leu Thr Pro Gly Thr Glu His Arg>
___c___c___c___c___c____RECOMBINANT LEUKOTOXIN PEPTIDE_c___c___c___c___c___c___>

1570          1580          1590          1600          1610          1620
       .       *      .      *      .      *      .      *      .      *      .      *
GAA CGC GTA CAA ACA GGT AAA TAT GAA TAT ATT ACC AAG CTC AAT ATT AAC CGT GTA GAT
CTT GCG CAT GTT TGT CCA TTT ATA CTT ATA TAA TGG TTC GAG TTA TAA TTG GCA CAT CTA
Glu Arg Val Gln Thr Gly Lys Tyr Glu Tyr Ile Thr Lys Leu Asn Ile Asn Arg Val Asp>
___c___c___c___c___c____RECOMBINANT LEUKOTOXIN PEPTIDE_c___c___c___c___c___c___>

1630          1640          1650          1660          1670          1680
       .       *      .      *      .      *      .      *      .      *      .      *
AGC TGG AAA ATT ACA GAT GGT GCA GCA AGT TCT ACC TTT GAT TTA ACT AAC GTT GTT CAG
TCG ACC TTT TAA TGT CTA CCA CGT CGT TCA AGA TGG AAA CTA AAT TGA TTG CAA CAA GTC
Ser Trp Lys Ile Thr Asp Gly Ala Ala Ser Ser Thr Phe Asp Leu Thr Asn Val Val Gln>
___c___c___c___c___c____RECOMBINANT LEUKOTOXIN PEPTIDE_c___c___c___c___c___c___>

1690          1700          1710          1720          1730          1740
       .       *      .      *      .      *      .      *      .      *      .      *
CGT ATT GGT ATT GAA TTA GAC AAT GCT GGA AAT GTA ACT AAA ACC AAA GAA ACA AAA ATT
GCA TAA CCA TAA CTT AAT CTG TTA CGA CCT TTA CAT TGA TTT TGG TTT CTT TGT TTT TAA
Arg Ile Gly Ile Glu Leu Asp Asn Ala Gly Asn Val Thr Lys Thr Lys Glu Thr Lys Ile>
___c___c___c___c___c____RECOMBINANT LEUKOTOXIN PEPTIDE_c___c___c___c___c___c___>

1750          1760          1770          1780          1790          1800
       .       *      .      *      .      *      .      *      .      *      .      *
ATT GCC AAA CTT GGT GAA GGT GAT GAC AAC GTA TTT GTT GGT TCT GGT ACG ACG GAA ATT
TAA CGG TTT GAA CCA CTT CCA CTA CTG TTG CAT AAA CAA CCA AGA CCA TGC TGC CTT TAA
Ile Ala Lys Leu Gly Glu Gly Asp Asp Asn Val Phe Val Gly Ser Gly Thr Thr Glu Ile>
___c___c___c___c___c____RECOMBINANT LEUKOTOXIN PEPTIDE_c___c___c___c___c___c___>

1810          1820          1830          1840          1850          1860
       .       *      .      *      .      *      .      *      .      *      .      *
GAT GGC GGT GAA GGT TAC GAC CGA GTT CAC TAT AGC CGT GGA AAC TAT GGT GCT TTA ACT
CTA CCG CCA CTT CCA ATG CTG GCT CAA GTG ATA TCG GCA CCT TTG ATA CCA CGA AAT TGA
Asp Gly Gly Glu Gly Tyr Asp Arg Val His Tyr Ser Arg Gly Asn Tyr Gly Ala Leu Thr>
___c___c___c___c___c____RECOMBINANT LEUKOTOXIN PEPTIDE_c___c___c___c___c___c___>

1870          1880          1890          1900          1910          1920
       .       *      .      *      .      *      .      *      .      *      .      *
ATT GAT GCA ACC AAA GAG ACC GAG CAA GGT AGT TAT ACC GTA AAT CGT TTC GTA GAA ACC
TAA CTA CGT TGG TTT CTC TGG CTC GTT CCA TCA ATA TGG CAT TTA GCA AAG CAT CTT TGG
Ile Asp Ala Thr Lys Glu Thr Glu Gln Gly Ser Tyr Thr Val Asn Arg Phe Val Glu Thr>
___c___c___c___c___c____RECOMBINANT LEUKOTOXIN PEPTIDE_c___c___c___c___c___c___>
```

FIG.5D

```
              1930        1940        1950        1960        1970        1980
                *           *           *           *           *           *
       GGT AAA GCA CTA CAC GAA GTG ACT TCA ACC CAT ACC GCA TTA GTG GGC AAC CGT GAA GAA
       CCA TTT CGT GAT GTG CTT CAC TGA AGT TGG GTA TGG CGT AAT CAC CCG TTG GCA CTT CTT
       Gly Lys Ala Leu His Glu Val Thr Ser Thr His Thr Ala Leu Val Gly Asn Arg Glu Glu>
       ___c___c___c___c___c_____RECOMBINANT LEUKOTOXIN PEPTIDE_c___c___c___c___c___c___>

1990        2000        2010        2020        2030        2040
                *           *           *           *           *           *
       AAA ATA GAA TAT CGT CAT AGC AAT AAC CAG CAC CAT GCC GGT TAT TAC ACC AAA GAT ACC
       TTT TAT CTT ATA GCA GTA TCG TTA TTG GTC GTG GTA CGG CCA ATA ATG TGG TTT CTA TGG
       Lys Ile Glu Tyr Arg His Ser Asn Asn Gln His His Ala Gly Tyr Tyr Thr Lys Asp Thr>
       ___c___c___c___c___c_____RECOMBINANT LEUKOTOXIN PEPTIDE_c___c___c___c___c___c___>

2050        2060        2070        2080        2090        2100
                *           *           *           *           *           *
       TTG AAA GCT GTT GAA GAA ATT ATC GGT ACA TCA CAT AAC GAT ATC TTT AAA GGT AGT AAG
       AAC TTT CGA CAA CTT CTT TAA TAG CCA TGT AGT GTA TTG CTA TAG AAA TTT CCA TCA TTC
       Leu Lys Ala Val Glu Glu Ile Ile Gly Thr Ser His Asn Asp Ile Phe Lys Gly Ser Lys>
       ___c___c___c___c___c_____RECOMBINANT LEUKOTOXIN PEPTIDE_c___c___c___c___c___c___>

2110        2120        2130        2140        2150        2160
                *           *           *           *           *           *
       TTC AAT GAT GCC TTT AAC GGT GGT GAT GGT GTC GAT ACT ATT GAC GGT AAC GAC GGC AAT
       AAG TTA CTA CGG AAA TTG CCA CCA CTA CCA CAG CTA TGA TAA CTG CCA TTG CTG CCG TTA
       Phe Asn Asp Ala Phe Asn Gly Gly Asp Gly Val Asp Thr Ile Asp Gly Asn Asp Gly Asn>
       ___c___c___c___c___c_____RECOMBINANT LEUKOTOXIN PEPTIDE_c___c___c___c___c___c___>

2170        2180        2190        2200        2210        2220
                *           *           *           *           *           *
       GAC CGC TTA TTT GGT GGT AAA GGC GAT GAT ATT CTC GAT GGT GGA AAT GGT GAT GAT TTT
       CTG GCG AAT AAA CCA CCA TTT CCG CTA CTA TAA GAG CTA CCA CCT TTA CCA CTA CTA AAA
       Asp Arg Leu Phe Gly Gly Lys Gly Asp Asp Ile Leu Asp Gly Gly Asn Gly Asp Asp Phe>
       ___c___c___c___c___c_____RECOMBINANT LEUKOTOXIN PEPTIDE_c___c___c___c___c___c___>

2230        2240        2250        2260        2270        2280
                *           *           *           *           *           *
       ATC GAT GGC GGT AAA GGC AAC GAC CTA TTA CAC GGT GGC AAG GGC GAT GAT ATT TTC GTT
       TAG CTA CCG CCA TTT CCG TTG CTG GAT AAT GTG CCA CCG TTC CCG CTA CTA TAA AAG CAA
       Ile Asp Gly Gly Lys Gly Asn Asp Leu Leu His Gly Gly Lys Gly Asp Asp Ile Phe Val>
       ___c___c___c___c___c_____RECOMBINANT LEUKOTOXIN PEPTIDE_c___c___c___c___c___c___>

2290        2300        2310        2320        2330        2340
                *           *           *           *           *           *
       CAC CGT AAA GGC GAT GGT AAT GAT ATT ATT ACC GAT TCT GAC GGC AAT GAT AAA TTA TCA
       GTG GCA TTT CCG CTA CCA TTA CTA TAA TAA TGG CTA AGA CTG CCG TTA CTA TTT AAT AGT
       His Arg Lys Gly Asp Gly Asn Asp Ile Ile Thr Asp Ser Asp Gly Asn Asp Lys Leu Ser>
       ___c___c___c___c___c_____RECOMBINANT LEUKOTOXIN PEPTIDE_c___c___c___c___c___c___>

2350        2360        2370        2380        2390        2400
                *           *           *           *           *           *
       TTC TCT GAT TCG AAC TTA AAA GAT TTA ACA TTT GAA AAA GTT AAA CAT AAT CTT GTC ATC
       AAG AGA CTA AGC TTG AAT TTT CTA AAT TGT AAA CTT TTT CAA TTT GTA TTA GAA CAG TAG
       Phe Ser Asp Ser Asn Leu Lys Asp Leu Thr Phe Glu Lys Val Lys His Asn Leu Val Ile>
       ___c___c___c___c___c_____RECOMBINANT LEUKOTOXIN PEPTIDE_c___c___c___c___c___c___>
```

FIG.5E

```
         2410          2420          2430          2440          2450          2460
           *             *             *             *             *             *
ACG AAT AGC AAA AAA GAG AAA GTG ACC ATT CAA AAC TGG TTC CGA GAG GCT GAT TTT GCT
TGC TTA TCG TTT TTT CTC TTT CAC TGG TAA GTT TTG ACC AAG GCT CTC CGA CTA AAA CGA
Thr Asn Ser Lys Lys Glu Lys Val Thr Ile Gln Asn Trp Phe Arg Glu Ala Asp Phe Ala>
___c___c___c___c___c____RECOMBINANT LEUKOTOXIN PEPTIDE_c___c___c___c___c___c___>

2470          2480          2490          2500          2510          2520
           *             *             *             *             *             *
AAA GAA GTG CCT AAT TAT AAA GCA ACT AAA GAT GAG AAA ATC GAA GAA ATC ATC GGT CAA
TTT CTT CAC GGA TTA ATA TTT CGT TGA TTT CTA CTC TTT TAG CTT CTT TAG TAG CCA GTT
Lys Glu Val Pro Asn Tyr Lys Ala Thr Lys Asp Glu Lys Ile Glu Glu Ile Ile Gly Gln>
___c___c___c___c___c____RECOMBINANT LEUKOTOXIN PEPTIDE_c___c___c___c___c___c___>

2530          2540          2550          2560          2570          2580
           *             *             *             *             *             *
AAT GGC GAG CGG ATC ACC TCA AAG CAA GTT GAT GAT CTT ATC GCA AAA GGT AAC GGC AAA
TTA CCG CTC GCC TAG TGG AGT TTC GTT CAA CTA CTA GAA TAG CGT TTT CCA TTG CCG TTT
Asn Gly Glu Arg Ile Thr Ser Lys Gln Val Asp Asp Leu Ile Ala Lys Gly Asn Gly Lys>
___c___c___c___c___c____RECOMBINANT LEUKOTOXIN PEPTIDE_c___c___c___c___c___c___>

2590          2600          2610          2620          2630          2640
           *             *             *             *             *             *
ATT ACC CAA GAT GAG CTA TCA AAA GTT GTT GAT AAC TAT GAA TTG CTC AAA CAT AGC AAA
TAA TGG GTT CTA CTC GAT AGT TTT CAA CAA CTA TTG ATA CTT AAC GAG TTT GTA TCG TTT
Ile Thr Gln Asp Glu Leu Ser Lys Val Val Asp Asn Tyr Glu Leu Leu Lys His Ser Lys>
___c___c___c___c___c____RECOMBINANT LEUKOTOXIN PEPTIDE_c___c___c___c___c___c___>

2650          2660          2670          2680          2690          2700
           *             *             *             *             *             *
AAT GTG ACA AAC AGC TTA GAT AAG TTA ATC TCA TCT GTA AGT GCA TTT ACC TCG TCT AAT
TTA CAC TGT TTG TCG AAT CTA TTC AAT TAG AGT AGA CAT TCA CGT AAA TGG AGC AGA TTA
Asn Val Thr Asn Ser Leu Asp Lys Leu Ile Ser Ser Val Ser Ala Phe Thr Ser Ser Asn>
___c___c___c___c___c____RECOMBINANT LEUKOTOXIN PEPTIDE_c___c___c___c___c___c___>

2710          2720          2730          2740          2750          2760
           *             *             *             *             *             *
GAT TCG AGA AAT GTA TTA GTG GCT CCA ACT TCA ATG TTG GAT CAA AGT TTA TCT TCT CTT
CTA AGC TCT TTA CAT AAT CAC CGA GGT TGA AGT TAC AAC CTA GTT TCA AAT AGA AGA GAA
Asp Ser Arg Asn Val Leu Val Ala Pro Thr Ser Met Leu Asp Gln Ser Leu Ser Ser Leu>
___c___c___c___c___c____RECOMBINANT LEUKOTOXIN PEPTIDE_c___c___c___c___c___c___>

2770          2780          2790
           *             *             *       *
CAA TTT GCT AGG GGA TCC TAG CTAGCTAGCCATGG
GTT AAA CGA TCC CCT AGG ATC GATCGATCGGTACC
Gln Phe Ala Arg Gly Ser End>
___RECOMBINANT LEUKOTOX____>
            _b____VECTOR SEQUENCE_____>
```

FIG.5F

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 2794 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION: 1..2778

(xi) SEQUENCE DESCRIPTION: SEQ ID NO:1:

```
ATG GCT ACT GTT ATA GAT CTA AGC TTC CCA AAA ACT GGG GCA AAA AAA        48
Met Ala Thr Val Ile Asp Leu Ser Phe Pro Lys Thr Gly Ala Lys Lys
 1               5                  10                  15

ATT ATC CTC TAT ATT CCC CAA AAT TAC CAA TAT GAT ACT GAA CAA GGT        96
Ile Ile Leu Tyr Ile Pro Gln Asn Tyr Gln Tyr Asp Thr Glu Gln Gly
             20                  25                  30

AAT GGT TTA CAG GAT TTA GTC AAA GCG GCC GAA GAG TTG GGG ATT GAG       144
Asn Gly Leu Gln Asp Leu Val Lys Ala Ala Glu Glu Leu Gly Ile Glu
         35                  40                  45

GTA CAA AGA GAA GAA CGC AAT AAT ATT GCA ACA GCT CAA ACC AGT TTA       192
Val Gln Arg Glu Glu Arg Asn Asn Ile Ala Thr Ala Gln Thr Ser Leu
     50                  55                  60

GGC ACG ATT CAA ACC GCT ATT GGC TTA ACT GAG CGT GGC ATT GTG TTA       240
Gly Thr Ile Gln Thr Ala Ile Gly Leu Thr Glu Arg Gly Ile Val Leu
 65                  70                  75                  80

TCC GCT CCA CAA ATT GAT AAA TTG CTA CAG AAA ACT AAA GCA GGC CAA       288
Ser Ala Pro Gln Ile Asp Lys Leu Leu Gln Lys Thr Lys Ala Gly Gln
                 85                  90                  95

GCA TTA GGT TCT GCC GAA AGC ATT GTA CAA AAT GCA AAT AAA GCC AAA       336
Ala Leu Gly Ser Ala Glu Ser Ile Val Gln Asn Ala Asn Lys Ala Lys
            100                 105                 110

ACT GTA TTA TCT GGC ATT CAA TCT ATT TTA GGC TCA GTA TTG GCT GGA       384
Thr Val Leu Ser Gly Ile Gln Ser Ile Leu Gly Ser Val Leu Ala Gly
        115                 120                 125

ATG GAT TTA GAT GAG GCC TTA CAG AAT AAC AGC AAC CAA CAT GCT CTT       432
Met Asp Leu Asp Glu Ala Leu Gln Asn Asn Ser Asn Gln His Ala Leu
    130                 135                 140

GCT AAA GCT GGC TTG GAG CTA ACA AAT TCA TTA ATT GAA AAT ATT GCT       480
Ala Lys Ala Gly Leu Glu Leu Thr Asn Ser Leu Ile Glu Asn Ile Ala
145                 150                 155                 160
```

| | | |
|---|---|---|
| AAT TCA GTA AAA ACA CTT GAC GAA TTT GGT GAG CAA ATT AGT CAA TTT<br>Asn Ser Val Lys Thr Leu Asp Glu Phe Gly Glu Gln Ile Ser Gln Phe<br>              165                      170                      175 | 528 |
| GGT TCA AAA CTA CAA AAT ATC AAA GGC TTA GGG ACT TTA GGA GAC AAA<br>Gly Ser Lys Leu Gln Asn Ile Lys Gly Leu Gly Thr Leu Gly Asp Lys<br>            180                      185                      190 | 576 |
| CTC AAA AAT ATC GGT GGA CTT GAT AAA GCT GGC CTT GGT TTA GAT GTT<br>Leu Lys Asn Ile Gly Gly Leu Asp Lys Ala Gly Leu Gly Leu Asp Val<br>               195                      200                    205 | 624 |
| ATC TCA GGG CTA TTA TCG GGC GCA ACA GCT GCA CTT GTA CTT GCA GAT<br>Ile Ser Gly Leu Leu Ser Gly Ala Thr Ala Ala Leu Val Leu Ala Asp<br>210                        215                          220 | 672 |
| AAA AAT GCT TCA ACA GCT AAA AAA GTG GGT GCG GGT TTT GAA TTG GCA<br>Lys Asn Ala Ser Thr Ala Lys Lys Val Gly Ala Gly Phe Glu Leu Ala<br>225                        230                        235              240 | 720 |
| AAC CAA GTT GTT GGT AAT ATT ACC AAA GCC GTT TCT TCT TAC ATT TTA<br>Asn Gln Val Val Gly Asn Ile Thr Lys Ala Val Ser Ser Tyr Ile Leu<br>                      245                      250                    255 | 768 |
| GCC CAA CGT GTT GCA GCA GGT TTA TCT TCA ACT GGG CCT GTG GCT GCT<br>Ala Gln Arg Val Ala Ala Gly Leu Ser Ser Thr Gly Pro Val Ala Ala<br>            260                      265                      270 | 816 |
| TTA ATT GCT TCT ACT GTT TCT CTT GCG ATT AGC CCA TTA GCA TTT GCC<br>Leu Ile Ala Ser Thr Val Ser Leu Ala Ile Ser Pro Leu Ala Phe Ala<br>            275                      280                    285 | 864 |
| GGT ATT GCC GAT AAA TTT AAT CAT GCA AAA AGT TTA GAG AGT TAT GCC<br>Gly Ile Ala Asp Lys Phe Asn His Ala Lys Ser Leu Glu Ser Tyr Ala<br>            290                      295                    300 | 912 |
| GAA CGC TTT AAA AAA TTA GGC TAT GAC GGA GAT AAT TTA TTA GCA GAA<br>Glu Arg Phe Lys Lys Leu Gly Tyr Asp Gly Asp Asn Leu Leu Ala Glu<br>305                      310                      315              320 | 960 |
| TAT CAG CGG GGA ACA GGG ACT ATT GAT GCA TCG GTT ACT GCA ATT AAT<br>Tyr Gln Arg Gly Thr Gly Thr Ile Asp Ala Ser Val Thr Ala Ile Asn<br>                      325                      330                    335 | 1008 |
| ACC GCA TTG GCC GCT ATT GCT GGT GGT GTG TCT GCT GCT GCA GCC GGC<br>Thr Ala Leu Ala Ala Ile Ala Gly Gly Val Ser Ala Ala Ala Ala Gly<br>               340                      345                    350 | 1056 |
| TCG GTT ATT GCT TCA CCG ATT GCC TTA TTA GTA TCT GGG ATT ACC GGT<br>Ser Val Ile Ala Ser Pro Ile Ala Leu Leu Val Ser Gly Ile Thr Gly<br>            355                      360                    365 | 1104 |
| GTA ATT TCT ACG ATT CTG CAA TAT TCT AAA CAA GCA ATG TTT GAG CAC<br>Val Ile Ser Thr Ile Leu Gln Tyr Ser Lys Gln Ala Met Phe Glu His<br>370                        375                        380 | 1152 |
| GTT GCA AAT AAA ATT CAT AAC AAA ATT GTA GAA TGG GAA AAA AAT AAT<br>Val Ala Asn Lys Ile His Asn Lys Ile Val Glu Trp Glu Lys Asn Asn<br>385                      390                      395              400 | 1200 |
| CAC GGT AAG AAC TAC TTT GAA AAT GGT TAC GAT GCC CGT TAT CTT GCG<br>His Gly Lys Asn Tyr Phe Glu Asn Gly Tyr Asp Ala Arg Tyr Leu Ala<br>                      405                      410                    415 | 1248 |
| AAT TTA CAA GAT AAT ATG AAA TTC TTA CTG AAC TTA AAC AAA GAG TTA<br>Asn Leu Gln Asp Asn Met Lys Phe Leu Leu Asn Leu Asn Lys Glu Leu<br>               420                      425                    430 | 1296 |
| CAG GCA GAA CGT GTC ATC GCT ATT ACT CAG CAG CAA TGG GAT AAC AAC<br>Gln Ala Glu Arg Val Ile Ala Ile Thr Gln Gln Gln Trp Asp Asn Asn<br>            435                      440                    445 | 1344 |
| ATT GGT GAT TTA GCT GGT ATT AGC CGT TTA GGT GAA AAA GTC CTT AGT<br>Ile Gly Asp Leu Ala Gly Ile Ser Arg Leu Gly Glu Lys Val Leu Ser<br>               450                      455                    460 | 1392 |
| GGT AAA GCC TAT GTG GAT GCG TTT GAA GAA GGC AAA CAC ATT AAA GCC<br>Gly Lys Ala Tyr Val Asp Ala Phe Glu Glu Gly Lys His Ile Lys Ala<br>465                      470                      475                    480 | 1440 |

```
GAT AAA TTA GTA CAG TTG GAT TCG GCA AAC GGT ATT ATT GAT GTG AGT       1488
Asp Lys Leu Val Gln Leu Asp Ser Ala Asn Gly Ile Ile Asp Val Ser
                485                 490                 495

AAT TCG GGT AAA GCG AAA ACT CAG CAT ATC TTA TTC AGA ACG CCA TTA       1536
Asn Ser Gly Lys Ala Lys Thr Gln His Ile Leu Phe Arg Thr Pro Leu
            500                 505                 510

TTG ACG CCG GGA ACA GAG CAT CGT GAA CGC GTA CAA ACA GGT AAA TAT       1584
Leu Thr Pro Gly Thr Glu His Arg Glu Arg Val Gln Thr Gly Lys Tyr
        515                 520                 525

GAA TAT ATT ACC AAG CTC AAT ATT AAC CGT GTA GAT AGC TGG AAA ATT       1632
Glu Tyr Ile Thr Lys Leu Asn Ile Asn Arg Val Asp Ser Trp Lys Ile
530                 535                 540

ACA GAT GGT GCA GCA AGT TCT ACC TTT GAT TTA ACT AAC GTT GTT CAG       1680
Thr Asp Gly Ala Ala Ser Ser Thr Phe Asp Leu Thr Asn Val Val Gln
545                 550                 555                 560

CGT ATT GGT ATT GAA TTA GAC AAT GCT GGA AAT GTA ACT AAA ACC AAA       1728
Arg Ile Gly Ile Glu Leu Asp Asn Ala Gly Asn Val Thr Lys Thr Lys
                565                 570                 575

GAA ACA AAA ATT ATT GCC AAA CTT GGT GAA GGT GAT GAC AAC GTA TTT       1776
Glu Thr Lys Ile Ile Ala Lys Leu Gly Glu Gly Asp Asp Asn Val Phe
            580                 585                 590

GTT GGT TCT GGT ACG ACG GAA ATT GAT GGC GGT GAA GGT TAC GAC CGA       1824
Val Gly Ser Gly Thr Thr Glu Ile Asp Gly Gly Glu Gly Tyr Asp Arg
        595                 600                 605

GTT CAC TAT AGC CGT GGA AAC TAT GGT GCT TTA ACT ATT GAT GCA ACC       1872
Val His Tyr Ser Arg Gly Asn Tyr Gly Ala Leu Thr Ile Asp Ala Thr
610                 615                 620

AAA GAG ACC GAG CAA GGT AGT TAT ACC GTA AAT CGT TTC GTA GAA ACC       1920
Lys Glu Thr Glu Gln Gly Ser Tyr Thr Val Asn Arg Phe Val Glu Thr
625                 630                 635                 640

GGT AAA GCA CTA CAC GAA GTG ACT TCA ACC CAT ACC GCA TTA GTG GGC       1968
Gly Lys Ala Leu His Glu Val Thr Ser Thr His Thr Ala Leu Val Gly
                645                 650                 655

AAC CGT GAA GAA AAA ATA GAA TAT CGT CAT AGC AAT AAC CAG CAC CAT       2016
Asn Arg Glu Glu Lys Ile Glu Tyr Arg His Ser Asn Asn Gln His His
            660                 665                 670

GCC GGT TAT TAC ACC AAA GAT ACC TTG AAA GCT GTT GAA GAA ATT ATC       2064
Ala Gly Tyr Tyr Thr Lys Asp Thr Leu Lys Ala Val Glu Glu Ile Ile
        675                 680                 685

GGT ACA TCA CAT AAC GAT ATC TTT AAA GGT AGT AAG TTC AAT GAT GCC       2112
Gly Thr Ser His Asn Asp Ile Phe Lys Gly Ser Lys Phe Asn Asp Ala
690                 695                 700

TTT AAC GGT GGT GAT GGT GTC GAT ACT ATT GAC GGT AAC GAC GGC AAT       2160
Phe Asn Gly Gly Asp Gly Val Asp Thr Ile Asp Gly Asn Asp Gly Asn
705                 710                 715                 720

GAC CGC TTA TTT GGT GGT AAA GGC GAT GAT ATT CTC GAT GGT GGA AAT       2208
Asp Arg Leu Phe Gly Gly Lys Gly Asp Asp Ile Leu Asp Gly Gly Asn
                725                 730                 735

GGT GAT GAT TTT ATC GAT GGC GGT AAA GGC AAC GAC CTA TTA CAC GGT       2256
Gly Asp Asp Phe Ile Asp Gly Gly Lys Gly Asn Asp Leu Leu His Gly
            740                 745                 750

GGC AAG GGC GAT GAT ATT TTC GTT CAC CGT AAA GGC GAT GGT AAT GAT       2304
Gly Lys Gly Asp Asp Ile Phe Val His Arg Lys Gly Asp Gly Asn Asp
        755                 760                 765

ATT ATT ACC GAT TCT GAC GGC AAT GAT AAA TTA TCA TTC TCT GAT TCG       2352
Ile Ile Thr Asp Ser Asp Gly Asn Asp Lys Leu Ser Phe Ser Asp Ser
770                 775                 780

AAC TTA AAA GAT TTA ACA TTT GAA AAA GTT AAA CAT AAT CTT GTC ATC       2400
Asn Leu Lys Asp Leu Thr Phe Glu Lys Val Lys His Asn Leu Val Ile
785                 790                 795                 800
```

```
ACG AAT AGC AAA AAA GAG AAA GTG ACC ATT CAA AAC TGG TTC CGA GAG         2448
Thr Asn Ser Lys Lys Glu Lys Val Thr Ile Gln Asn Trp Phe Arg Glu
            805                 810                 815

GCT GAT TTT GCT AAA GAA GTG CCT AAT TAT AAA GCA ACT AAA GAT GAG         2496
Ala Asp Phe Ala Lys Glu Val Pro Asn Tyr Lys Ala Thr Lys Asp Glu
            820                 825                 830

AAA ATC GAA GAA ATC ATC GGT CAA AAT GGC GAG CGG ATC ACC TCA AAG         2544
Lys Ile Glu Glu Ile Ile Gly Gln Asn Gly Glu Arg Ile Thr Ser Lys
            835                 840                 845

CAA GTT GAT GAT CTT ATC GCA AAA GGT AAC GGC AAA ATT ACC CAA GAT         2592
Gln Val Asp Asp Leu Ile Ala Lys Gly Asn Gly Lys Ile Thr Gln Asp
    850                 855                 860

GAG CTA TCA AAA GTT GTT GAT AAC TAT GAA TTG CTC AAA CAT AGC AAA         2640
Glu Leu Ser Lys Val Val Asp Asn Tyr Glu Leu Leu Lys His Ser Lys
865                 870                 875                 880

AAT GTG ACA AAC AGC TTA GAT AAG TTA ATC TCA TCT GTA AGT GCA TTT         2688
Asn Val Thr Asn Ser Leu Asp Lys Leu Ile Ser Ser Val Ser Ala Phe
                885                 890                 895

ACC TCG TCT AAT GAT TCG AGA AAT GTA TTA GTG GCT CCA ACT TCA ATG         2736
Thr Ser Ser Asn Asp Ser Arg Asn Val Leu Val Ala Pro Thr Ser Met
                900                 905                 910

TTG GAT CAA AGT TTA TCT TCT CTT CAA TTT GCT AGG GGA TCC                 2778
Leu Asp Gln Ser Leu Ser Ser Leu Gln Phe Ala Arg Gly Ser
            915                 920                 925

TAGCTAGCTA GCCATG                                                       2794
```

(2) INFORMATION FOR SEQ ID NO:2:

(i) SEQUENCE CHARACTERISTICS:
        (A) LENGTH: 926 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Thr Val Ile Asp Leu Ser Phe Pro Lys Thr Gly Ala Lys Lys
 1               5                  10                  15

Ile Ile Leu Tyr Ile Pro Gln Asn Tyr Gln Tyr Asp Thr Glu Gln Gly
            20                  25                  30

Asn Gly Leu Gln Asp Leu Val Lys Ala Ala Glu Glu Leu Gly Ile Glu
        35                  40                  45

Val Gln Arg Glu Glu Arg Asn Asn Ile Ala Thr Ala Gln Thr Ser Leu
    50                  55                  60

Gly Thr Ile Gln Thr Ala Ile Gly Leu Thr Glu Arg Gly Ile Val Leu
65                  70                  75                  80

Ser Ala Pro Gln Ile Asp Lys Leu Leu Gln Lys Thr Lys Ala Gly Gln
                85                  90                  95

Ala Leu Gly Ser Ala Glu Ser Ile Val Gln Asn Ala Asn Lys Ala Lys
            100                 105                 110

Thr Val Leu Ser Gly Ile Gln Ser Ile Leu Gly Ser Val Leu Ala Gly
        115                 120                 125

Met Asp Leu Asp Glu Ala Leu Gln Asn Asn Ser Asn Gln His Ala Leu
    130                 135                 140

Ala Lys Ala Gly Leu Glu Leu Thr Asn Ser Leu Ile Glu Asn Ile Ala
145                 150                 155                 160

Asn Ser Val Lys Thr Leu Asp Glu Phe Gly Glu Gln Ile Ser Gln Phe
                165                 170                 175
```

```
Gly Ser Lys Leu Gln Asn Ile Lys Gly Leu Gly Thr Leu Gly Asp Lys
            180                 185                 190

Leu Lys Asn Ile Gly Gly Leu Asp Lys Ala Gly Leu Gly Leu Asp Val
        195                 200                 205

Ile Ser Gly Leu Leu Ser Gly Ala Thr Ala Ala Leu Val Leu Ala Asp
    210                 215                 220

Lys Asn Ala Ser Thr Ala Lys Lys Val Gly Ala Gly Phe Glu Leu Ala
225                 230                 235                 240

Asn Gln Val Val Gly Asn Ile Thr Lys Ala Val Ser Ser Tyr Ile Leu
                245                 250                 255

Ala Gln Arg Val Ala Ala Gly Leu Ser Ser Thr Gly Pro Val Ala Ala
            260                 265                 270

Leu Ile Ala Ser Thr Val Ser Leu Ala Ile Ser Pro Leu Ala Phe Ala
        275                 280                 285

Gly Ile Ala Asp Lys Phe Asn His Ala Lys Ser Leu Glu Ser Tyr Ala
    290                 295                 300

Glu Arg Phe Lys Lys Leu Gly Tyr Asp Gly Asp Asn Leu Leu Ala Glu
305                 310                 315                 320

Tyr Gln Arg Gly Thr Gly Thr Ile Asp Ala Ser Val Thr Ala Ile Asn
                325                 330                 335

Thr Ala Leu Ala Ala Ile Ala Gly Gly Val Ser Ala Ala Ala Ala Gly
            340                 345                 350

Ser Val Ile Ala Ser Pro Ile Ala Leu Leu Val Ser Gly Ile Thr Gly
        355                 360                 365

Val Ile Ser Thr Ile Leu Gln Tyr Ser Lys Gln Ala Met Phe Glu His
    370                 375                 380

Val Ala Asn Lys Ile His Asn Lys Ile Val Glu Trp Glu Lys Asn Asn
385                 390                 395                 400

His Gly Lys Asn Tyr Phe Glu Asn Gly Tyr Asp Ala Arg Tyr Leu Ala
                405                 410                 415

Asn Leu Gln Asp Asn Met Lys Phe Leu Leu Asn Leu Asn Lys Glu Leu
            420                 425                 430

Gln Ala Glu Arg Val Ile Ala Ile Thr Gln Gln Trp Asp Asn Asn
        435                 440                 445

Ile Gly Asp Leu Ala Gly Ile Ser Arg Leu Gly Glu Lys Val Leu Ser
    450                 455                 460

Gly Lys Ala Tyr Val Asp Ala Phe Glu Glu Lys His Ile Lys Ala
465                 470                 475                 480

Asp Lys Leu Val Gln Leu Asp Ser Ala Asn Gly Ile Ile Asp Val Ser
                485                 490                 495

Asn Ser Gly Lys Ala Lys Thr Gln His Ile Leu Phe Arg Thr Pro Leu
            500                 505                 510

Leu Thr Pro Gly Thr Glu His Arg Glu Arg Val Gln Thr Gly Lys Tyr
        515                 520                 525

Glu Tyr Ile Thr Lys Leu Asn Ile Asn Arg Val Asp Ser Trp Lys Ile
    530                 535                 540

Thr Asp Gly Ala Ala Ser Ser Thr Phe Asp Leu Thr Asn Val Val Gln
545                 550                 555                 560

Arg Ile Gly Ile Glu Leu Asp Asn Ala Gly Asn Val Thr Lys Thr Lys
                565                 570                 575

Glu Thr Lys Ile Ile Ala Lys Leu Gly Glu Gly Asp Asp Asn Val Phe
            580                 585                 590

Val Gly Ser Gly Thr Thr Glu Ile Asp Gly Gly Glu Gly Tyr Asp Arg
        595                 600                 605
```

```
Val His Tyr Ser Arg Gly Asn Tyr Gly Ala Leu Thr Ile Asp Ala Thr
        610                 615                 620

Lys Glu Thr Glu Gln Gly Ser Tyr Thr Val Asn Arg Phe Val Glu Thr
625                 630                 635                 640

Gly Lys Ala Leu His Glu Val Thr Ser Thr His Thr Ala Leu Val Gly
                645                 650                 655

Asn Arg Glu Glu Lys Ile Glu Tyr Arg His Ser Asn Asn Gln His His
        660                 665                 670

Ala Gly Tyr Tyr Thr Lys Asp Thr Leu Lys Ala Val Glu Glu Ile Ile
            675                 680                 685

Gly Thr Ser His Asn Asp Ile Phe Lys Gly Ser Lys Phe Asn Asp Ala
    690                 695                 700

Phe Asn Gly Gly Asp Gly Val Asp Thr Ile Asp Gly Asn Asp Gly Asn
705                 710                 715                 720

Asp Arg Leu Phe Gly Gly Lys Gly Asp Ile Leu Asp Gly Gly Asn
                725                 730                 735

Gly Asp Asp Phe Ile Asp Gly Gly Lys Gly Asn Asp Leu Leu His Gly
            740                 745                 750

Gly Lys Gly Asp Asp Ile Phe Val His Arg Lys Gly Asp Gly Asn Asp
        755                 760                 765

Ile Ile Thr Asp Ser Asp Gly Asn Asp Lys Leu Ser Phe Ser Asp Ser
    770                 775                 780

Asn Leu Lys Asp Leu Thr Phe Glu Lys Val Lys His Asn Leu Val Ile
785                 790                 795                 800

Thr Asn Ser Lys Lys Glu Lys Val Thr Ile Gln Asn Trp Phe Arg Glu
                805                 810                 815

Ala Asp Phe Ala Lys Glu Val Pro Asn Tyr Lys Ala Thr Lys Asp Glu
            820                 825                 830

Lys Ile Glu Glu Ile Ile Gly Gln Asn Gly Glu Arg Ile Thr Ser Lys
        835                 840                 845

Gln Val Asp Asp Leu Ile Ala Lys Gly Asn Gly Lys Ile Thr Gln Asp
    850                 855                 860

Glu Leu Ser Lys Val Val Asp Asn Tyr Glu Leu Leu Lys His Ser Lys
865                 870                 875                 880

Asn Val Thr Asn Ser Leu Asp Lys Leu Ile Ser Ser Val Ser Ala Phe
                885                 890                 895

Thr Ser Ser Asn Asp Ser Arg Asn Val Leu Val Ala Pro Thr Ser Met
            900                 905                 910

Leu Asp Gln Ser Leu Ser Ser Leu Gln Phe Ala Arg Gly Ser
        915                 920                 925
```

(2) INFORMATION FOR SEQ ID NO:3:

(i) SEQUENCE CHARACTERISTICS:
        (A) LENGTH: 1403 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Met Gly Thr Arg Leu Thr Thr Leu Ser Asn Gly Leu Lys Asn Thr Leu
1               5                   10                  15

Thr Ala Thr Lys Ser Gly Leu His Lys Ala Gly Gln Ser Leu Thr Gln
            20                  25                  30
```

```
Ala Gly Ser Ser Leu Lys Thr Gly Ala Lys Ile Ile Leu Tyr Ile
         35                  40                  45

Pro Gln Asn Tyr Gln Tyr Asp Thr Glu Gln Gly Asn Gly Leu Gln Asp
 50                  55                  60

Leu Val Lys Ala Ala Glu Leu Gly Ile Glu Val Gln Arg Glu Glu
 65                  70                  75                  80

Arg Asn Asn Ile Ala Thr Ala Gln Thr Ser Leu Gly Thr Ile Gln Thr
                 85                  90                  95

Ala Ile Gly Leu Thr Glu Arg Gly Ile Val Leu Ser Ala Pro Gln Ile
             100                 105                 110

Asp Lys Leu Leu Gln Lys Thr Lys Ala Gly Gln Ala Leu Gly Ser Ala
         115                 120                 125

Glu Ser Ile Val Gln Asn Ala Asn Lys Ala Lys Thr Val Leu Ser Gly
 130                 135                 140

Ile Gln Ser Ile Leu Gly Ser Val Leu Ala Gly Met Asp Leu Asp Glu
145                 150                 155                 160

Ala Leu Gln Asn Asn Ser Asn Gln His Ala Leu Ala Lys Ala Gly Leu
                 165                 170                 175

Glu Leu Thr Asn Ser Leu Ile Glu Asn Ile Ala Asn Ser Val Lys Thr
             180                 185                 190

Leu Asp Glu Phe Gly Glu Gln Ile Ser Gln Phe Gly Ser Lys Leu Gln
         195                 200                 205

Asn Ile Lys Gly Leu Gly Thr Leu Gly Asp Lys Leu Lys Asn Ile Gly
 210                 215                 220

Gly Leu Asp Lys Ala Gly Leu Gly Leu Asp Val Ile Ser Gly Leu Leu
225                 230                 235                 240

Ser Gly Ala Thr Ala Ala Leu Val Leu Ala Asp Lys Asn Ala Ser Thr
                 245                 250                 255

Ala Lys Lys Val Gly Ala Gly Phe Glu Leu Ala Asn Gln Val Val Gly
             260                 265                 270

Asn Ile Thr Lys Ala Val Ser Ser Tyr Ile Leu Ala Gln Arg Val Ala
         275                 280                 285

Ala Gly Leu Ser Ser Thr Gly Pro Val Ala Ala Leu Ile Ala Ser Thr
 290                 295                 300

Val Ser Leu Ala Ile Ser Pro Leu Ala Phe Ala Gly Ile Ala Asp Lys
305                 310                 315                 320

Phe Asn His Ala Lys Ser Leu Glu Ser Tyr Ala Glu Arg Phe Lys Lys
                 325                 330                 335

Leu Gly Tyr Asp Gly Asp Asn Leu Leu Ala Glu Tyr Gln Arg Gly Thr
             340                 345                 350

Gly Thr Ile Asp Ala Ser Val Thr Ala Ile Asn Thr Ala Leu Ala Ala
         355                 360                 365

Ile Ala Gly Gly Val Ser Ala Ala Gly Arg Arg Ile Arg Gly Ile
 370                 375                 380

Pro Gly Asp Pro Val Val Leu Gln Arg Arg Asp Trp Glu Asn Pro Gly
385                 390                 395                 400

Val Thr Gln Leu Asn Arg Leu Ala Ala His Pro Pro Phe Ala Ser Trp
                 405                 410                 415

Arg Asn Ser Glu Glu Ala Arg Thr Asp Arg Pro Ser Gln Gln Leu Arg
             420                 425                 430

Ser Leu Asn Gly Glu Trp Arg Phe Ala Trp Phe Pro Ala Pro Glu Ala
         435                 440                 445

Val Pro Glu Ser Trp Leu Glu Cys Asp Leu Pro Glu Ala Asp Thr Val
 450                 455                 460
```

-continued

```
Val Val Pro Ser Asn Trp Gln Met His Gly Tyr Asp Ala Pro Ile Tyr
465                 470                 475                 480

Thr Asn Val Thr Tyr Pro Ile Thr Val Asn Pro Pro Phe Val Pro Thr
            485                 490                 495

Glu Asn Pro Thr Gly Cys Tyr Ser Leu Thr Phe Asn Val Asp Glu Ser
            500                 505                 510

Trp Leu Gln Glu Gly Gln Thr Arg Ile Ile Phe Asp Gly Val Asn Ser
            515                 520                 525

Ala Phe His Leu Trp Cys Asn Gly Arg Trp Val Gly Tyr Gly Gln Asp
530                 535                 540

Ser Arg Leu Pro Ser Glu Phe Asp Leu Ser Ala Phe Leu Arg Ala Gly
545                 550                 555                 560

Glu Asn Arg Leu Ala Val Met Val Leu Arg Trp Ser Asp Gly Ser Tyr
                565                 570                 575

Leu Glu Asp Gln Asp Met Trp Arg Met Ser Gly Ile Phe Arg Asp Val
            580                 585                 590

Ser Leu Leu His Lys Pro Thr Thr Gln Ile Ser Asp Phe His Val Ala
            595                 600                 605

Thr Arg Phe Asn Asp Asp Phe Ser Arg Ala Val Leu Glu Ala Glu Val
610                 615                 620

Gln Met Cys Gly Glu Leu Arg Asp Tyr Leu Arg Val Thr Val Ser Leu
625                 630                 635                 640

Trp Gln Gly Glu Thr Gln Val Ala Ser Gly Thr Ala Pro Phe Gly Gly
                645                 650                 655

Glu Ile Ile Asp Glu Arg Gly Gly Tyr Ala Asp Arg Val Thr Leu Arg
            660                 665                 670

Leu Asn Val Glu Asn Pro Lys Leu Trp Ser Ala Glu Ile Pro Asn Leu
            675                 680                 685

Tyr Arg Ala Val Val Glu Leu His Thr Ala Asp Gly Thr Leu Ile Glu
690                 695                 700

Ala Glu Ala Cys Asp Val Gly Phe Arg Glu Val Arg Ile Glu Asn Gly
705                 710                 715                 720

Leu Leu Leu Leu Asn Gly Lys Pro Leu Leu Ile Arg Gly Val Asn Arg
                725                 730                 735

His Glu His His Pro Leu His Gly Gln Val Met Asp Glu Gln Thr Met
            740                 745                 750

Val Gln Asp Ile Leu Leu Met Lys Gln Asn Asn Phe Asn Ala Val Arg
            755                 760                 765

Cys Ser His Tyr Pro Asn His Pro Leu Trp Tyr Thr Leu Cys Asp Arg
770                 775                 780

Tyr Gly Leu Tyr Val Val Asp Glu Ala Asn Ile Glu Thr His Gly Met
785                 790                 795                 800

Val Pro Met Asn Arg Leu Thr Asp Asp Pro Arg Trp Leu Pro Ala Met
                805                 810                 815

Ser Glu Arg Val Thr Arg Met Val Gln Arg Asp Arg Asn His Pro Ser
            820                 825                 830

Val Ile Ile Trp Ser Leu Gly Asn Glu Ser Gly His Gly Ala Asn His
            835                 840                 845

Asp Ala Leu Tyr Arg Trp Ile Lys Ser Val Asp Pro Ser Arg Pro Val
850                 855                 860

Gln Tyr Glu Gly Gly Gly Ala Asp Thr Thr Ala Thr Asp Ile Ile Cys
865                 870                 875                 880
```

```
Pro Met Tyr Ala Arg Val Asp Glu Asp Gln Pro Phe Pro Ala Val Pro
                885                 890                 895

Lys Trp Ser Ile Lys Lys Trp Leu Ser Leu Pro Gly Glu Thr Arg Pro
                900                 905                 910

Leu Ile Leu Cys Glu Tyr Ala His Ala Met Gly Asn Ser Leu Gly Gly
                915                 920                 925

Phe Ala Lys Tyr Trp Gln Ala Phe Arg Gln Tyr Pro Arg Leu Gln Gly
                930                 935                 940

Gly Phe Val Trp Asp Trp Val Asp Gln Ser Leu Ile Lys Tyr Asp Glu
945                 950                 955                 960

Asn Gly Asn Pro Trp Ser Ala Tyr Gly Gly Asp Phe Gly Asp Thr Pro
                965                 970                 975

Asn Asp Arg Gln Phe Cys Met Asn Gly Leu Val Phe Ala Asp Arg Thr
                980                 985                 990

Pro His Pro Ala Leu Thr Glu Ala Lys His Gln Gln Gln Phe Phe Gln
                995                 1000                1005

Phe Arg Leu Ser Gly Gln Thr Ile Glu Val Thr Ser Glu Tyr Leu Phe
                1010                1015                1020

Arg His Ser Asp Asn Glu Leu Leu His Trp Met Val Ala Leu Asp Gly
1025                1030                1035                1040

Lys Pro Leu Ala Ser Gly Glu Val Pro Leu Asp Val Ala Pro Gln Gly
                1045                1050                1055

Lys Gln Leu Ile Glu Leu Pro Glu Leu Pro Gln Pro Glu Ser Ala Gly
                1060                1065                1070

Gln Leu Trp Leu Thr Val Arg Val Val Gln Pro Asn Ala Thr Ala Trp
                1075                1080                1085

Ser Glu Ala Gly His Ile Ser Ala Trp Gln Gln Trp Arg Leu Ala Glu
                1090                1095                1100

Asn Leu Ser Val Thr Leu Pro Ala Ala Ser His Ala Ile Pro His Leu
1105                1110                1115                1120

Thr Thr Ser Glu Met Asp Phe Cys Ile Glu Leu Gly Asn Lys Arg Trp
                1125                1130                1135

Gln Phe Asn Arg Gln Ser Gly Phe Leu Ser Gln Met Trp Ile Gly Asp
                1140                1145                1150

Lys Lys Gln Leu Leu Thr Pro Leu Arg Asp Gln Phe Thr Arg Ala Pro
                1155                1160                1165

Leu Asp Asn Asp Ile Gly Val Ser Glu Ala Thr Arg Ile Asp Pro Asn
                1170                1175                1180

Ala Trp Val Glu Arg Trp Lys Ala Ala Gly His Tyr Gln Ala Glu Ala
1185                1190                1195                1200

Ala Leu Leu Gln Cys Thr Ala Asp Thr Leu Ala Asp Ala Val Leu Ile
                1205                1210                1215

Thr Thr Ala His Ala Trp Gln His Gln Gly Lys Thr Leu Phe Ile Ser
                1220                1225                1230

Arg Lys Thr Tyr Arg Ile Asp Gly Ser Gly Gln Met Ala Ile Thr Val
                1235                1240                1245

Asp Val Glu Val Ala Ser Asp Thr Pro His Pro Ala Arg Ile Gly Leu
                1250                1255                1260

Asn Cys Gln Leu Ala Gln Val Ala Glu Arg Val Asn Trp Leu Gly Leu
1265                1270                1275                1280

Gly Pro Gln Glu Asn Tyr Pro Asp Arg Leu Thr Ala Ala Cys Phe Asp
                1285                1290                1295

Arg Trp Asp Leu Pro Leu Ser Asp Met Tyr Thr Pro Tyr Val Phe Pro
                1300                1305                1310
```

```
Ser Glu Asn Gly Leu Arg Cys Gly Thr Arg Glu Leu Asn Tyr Gly Pro
        1315                1320                1325

His Gln Trp Arg Gly Asp Phe Gln Phe Asn Ile Ser Arg Tyr Ser Gln
    1330                1335                1340

Gln Gln Leu Met Glu Thr Ser His Arg His Leu Leu His Ala Glu Glu
1345                1350                1355                1360

Gly Thr Trp Leu Asn Ile Asp Gly Phe His Met Gly Ile Gly Gly Asp
                1365                1370                1375

Asp Ser Trp Ser Pro Ser Val Ser Ala Glu Phe Gln Leu Ser Ala Gly
            1380                1385                1390

Arg Tyr His Tyr Gln Leu Val Trp Cys Gln Lys
        1395                1400
```

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Modified-site
        (B) LOCATION: 3
        (D) OTHER INFORMATION: /note= "The amino acid at this
            location can be either Lys, Asp, Val or Asn."

(ix) FEATURE:
        (A) NAME/KEY: Modified-site
        (B) LOCATION: 5
        (D) OTHER INFORMATION: /note= "The amino acid at this
            location can be either Lys, Asp, Val or Asn."

(xi) SEQUENCE DESCRIPTION: SEQ ID NO:4:

```
Gly Gly Xaa Gly Xaa Ala
1               5
```

(2) INFORMATION FOR SEQ ID NO:5:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Gly Gly Asn Gly Asp Asp Phe Ile Asp Gly Lys Gly Asn Asp Leu
1               5                   10                  15

Leu His Gly Gly
            20
```

(2) INFORMATION FOR SEQ ID NO:6:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:6:

```
Thr Met Asn Gly Asn Glu Phe Gln Thr Gly Gly Ile Gly Asn Leu Pro
1               5                   10                  15

Ile Arg Asn Trp Asn Ala Cys
                20
```

HAEMOPHILUS SOMNUS OUTER MEMBRANE PROTEIN EXTRACT ENRICHED WITH IRON-REGULATED PROTEINS

This is a Continuation of U.S. patent application Ser. No. 07/908,253, filed Jul. 2, 1992 which is now U.S. Pat. No. 5,534,256.

DESCRIPTION

TECHNICAL FIELD

The present invention relates generally to subunit antigens, vaccine compositions, and methods of administering the same. More particularly, the present invention relates to *Haemophilus somnus* outer membrane protein extracts enriched with iron-regulated proteins and to the use of such extracts in vaccine compositions to protect against *H. somnus* infections. Other bacterial antigens, such as leukotoxins, can be combined with the *H. somnus* vaccine to afford broad spectrum protection against a variety of diseases.

BACKGROUND OF THE INVENTION

*Haemophilus somnus* is a Gram negative bacterium which is related to several Actinobacillus species and appears to be identical to *Histophilus ovis* and *Haemophilus agni* (Philbey et al., *Aust. Vet. J.* (1991) 88:387–390). *H. somnus* causes a number of disease syndromes in animals. The bacterium is commonly associated with thromboembolic meningoencephalitis (ITEME), septicemia followed by sudden death, arthritis, and pneumonia (Corbeil, L. B., *Can. J. Vet. Res.* (1990) 54:S57–S62; Harris, F. W., and Janzen, E. D., *Can. Vet. J.* (1990) 30:816–822; Humphrey, J. D., and Stephens, L. R., *Vet. Bull.* (1983) 53:987–1004). These diseases can cause significant economic losses to the farm industry.

Current vaccines are either based on killed whole cells or on outer membrane protein (OMP) preparations. (See, e.g. U.S. Pat. Nos. 4,981,685, 4,877,613 and Stephens et al., *Am. J. Vet. Res.* (1984) 45:234–239). However, whole cell bacterins and surface protein extracts often contain immunosuppressive components which can render animals more susceptible to infection.

None of the above *H. somnus* preparations is enriched for iron-regulated proteins which are produced in iron-depleted environments. Certain iron-regulated proteins are immunogenic. For example, passive immunization with antibodies raised against iron-regulated outer membrane protein preparations has been shown to protect turkeys from *Escherichia coli* septicemia (Bolin, C. A., and Jensen, A. E., *Infect. Immun.* (1987) 55:1239–1242) and naturally occurring antibodies in human sera have been shown to react with iron-regulated outer membrane proteins of *E. coli* (Griffiths et al., *Infect. Immun.* (1985) 47:808–813). An iron-regulated protein has been identified in *H. influenzae* (Lee, B. C., *Infect. Immun.* (1992) 60:810–816).

In addition to Haemophilus infections, respiratory diseases associated with pathogenic microorganisms, particularly Pasteurella, and various stresses, such as transportation and overcrowding, are prevalent among feedlot cattle. One such disease is known as shipping fever which is characterized by sudden onset and pneumonia. Various bacteria and viruses have been isolated from affected animals including Pasteurella (particularly *P. haemolytica* and *P. multicoda*), bovine herpes virus 1, parainfluenza-3 virus, bovine respiratory syncytial virus and Mycoplasma species. For a general background on shipping fever see, Yates, W. D. G., *Can. J. Comp. Med.* (1982) 46:225–263.

*P. haemolytica* also causes enzootic pneumonia and can infect a wide range of animals, in addition to cattle, including sheep, swine, horses and fowl. *P. haemolytica* is also frequently found in the upper respiratory tract of healthy animals. Pneumonia develops when the bacteria infects the lungs of these animals. Protection against Pasteurella-associated diseases is therefore economically important to the agricultural industry.

There are two known biotypes of *P. haemolytica* designated A and T. There are also 12 recognized serotypes which have been isolated from ruminants. Biotype A, serotype 1 (referred to hereinafter as "A1") predominates in bovine pneumonia in North America (Shewen, P. E. and Wilkie, B. N., *Am. J. Vet. Res.* (1983) 44:715–719). However, antigens isolated from different serotypes appear to be somewhat cross-reactive (see, e.g., Donanchie et al., *J. Gen. Micro.* (1984) 130:1209–1216).

Previous vaccine preparations have included crude supernatant extracts from *P. haemolytica* (see, e.g., Shewen, P. E. and Wilkie, B. N., in can. *J. Vet. Res.* (1988) 52:30–36). These culture supernatants, however, contain various soluble surface antigens of the bacterium and produce variable results when administered to animals. Other preparations include capsular extracts obtained via sodium salicylate extraction (see, e.g., Donanchie et al. *J. Gen. Micro.* (1984) 130:1209–1216; U.S. Pat. No. 4,346,074), saline extracted antigens (see, e.g., Lessley et al., *Veterinary Immunology and Immunopathology* (1985) 10:279–296; Himmel et al.,*Am. J. Vet. Res.* (1982) 43:764–767), and modified live Pasteurella mutants.

Still other attempts at immunization have used a cytotoxin from *P. haemolytica* (see, e.g. Gentry et al., *Vet. Immunology and Immunopathology* (1985) 9:239–250; Conlon et al., *Infect. Immun.* (1991) 59:587–591; U.S. Pat. No. 4,957,739). This cytotoxin, which is a leukotoxin, is secreted by actively growing bacteria (Shewen, P. E., and Wilkie, B. N., *Infect. Immun.* (1987) 55:3233–3236). The gene encoding this cytotoxin has been cloned and expressed in bacterial cells (Lo et al., *Infect. Immun.* (1985) 50:667–67; U.S. Pat. No. 5,055,400; U.S. Pat. No. 4,957,739). Additionally, a truncated leukotoxin, which lacks the cytotoxic activity exhibited by the above cytotoxins, has been produced recombinantly and shown to be highly protective against shipping fever pneumonia (International Publication No. WO91/15237, published Oct. 17, 1991). However, none of these publications suggest the use of a leukotoxin in combination with an *H. somnus* antigenic preparation.

DISCLOSURE OF THE INVENTION

It has been discovered that subunit vaccines containing *H. somnus* OMP extracts enriched with iron-regulated proteins, offer significant protection from *H. somnus* infections. Other bacterial antigens, such as leukotoxin, can be added to the vaccine compositions, to additionally protect animals from respiratory diseases such as pneumonia, including shipping fever pneumonia. Based on these discoveries, the present invention can take several embodiments.

In one embodiment, the present invention is directed to a vaccine composition comprising a pharmaceutically acceptable vehicle and an outer membrane protein extract of *H. somnus* enriched with iron-regulated proteins.

In other embodiments, the subject vaccine includes an immunogenic amino acid sequence derived from a leukotoxin.

In yet another embodiment, the present invention is directed to a vaccine composition comprising:

a) a pharmaceutically acceptable vehicle;

b) an *H. somnus* outer membrane protein extract enriched with iron-regulated proteins;

c) LKT 352, having an amino acid sequence as depicted in FIG. 5; and d) a *P. haemolytica* saline extract.

In still another embodiment, the subject invention is directed to methods of treating or preventing *H. somnus* infection in a vertebrate subject comprising administering to the subject a therapeutically effective amount of the above vaccine compositions.

In another embodiment, the invention is directed to methods of treating or preventing *H. somnus* infection and Pasteurella infection in a vertebrate subject comprising administering to the subject a therapeutically effective amount of the combined vaccine compositions.

These and other embodiments of the subject invention will be apparent to one of skill in the art in view of the disclosure herein.

BRIEF DESCRIPTION OF THE FIGURES

FIG. 3 (SEQ ID NO:3) depicts the predicted amino acid sequence of the 1ktA::lacZ fusion protein from Plasmid pAA101. The portion representing the leukotoxin 1ktA protein is boxed.

FIGS. 5A through 5F (SEQ ID NOS:1–2) show the nucleotide sequence and predicted amino acid sequence of leukotoxin 352 (LKT 352) from plasmid pAA352. Both the structural gene for LKT 352 and the sequences of the flanking vector regions are shown.

DETAILED DESCRIPTION

Figure 1:
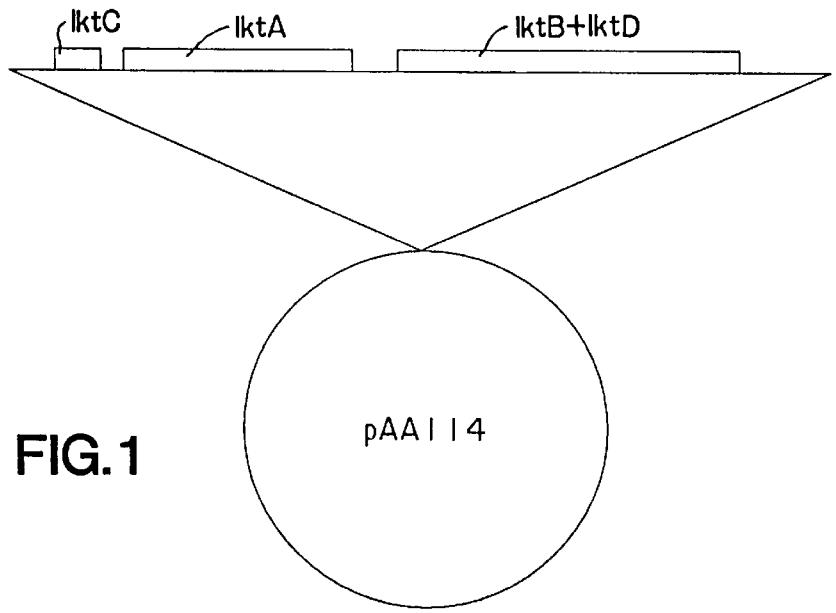
FIG. 1 depicts the structure of the leukotoxin gene of *P. haemolytica* cloned in *E. coli* (Plasmid pAA114).

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Second Edition (1989); *DNA Cloning*, Vols. I and II (D. N. Glover ed., 1985); *Oligonucleotide Synthesis* (M. J. Gait ed., 1984); Nucleic Acid Hybridization (B. D. Hames & S. J. Higgins eds., 1984); *Animal Cell Culture* (R. K. Freshney ed., 1986); *Immobilized Cells and Enzymes* (IRL press, 1986); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

A. Definitions

In describing the present invention, the following terms will be employed, and are intended to be defined as indicated below.

An "iron-regulated protein" is a protein which is produced in elevated quantities under iron-restricted growth conditions. Such an affect can be achieved by depriving growing cells of iron, either by eliminating iron sources from the media in which the cells are grown, or by adding chelating, or other iron-scavenging agents, to the media. Such agents are described in more detail below. The presence of iron-regulated proteins can be detected by comparing the composition of OMP extracts from cells grown under iron-restricted conditions (i.e., as assessed by column or gel chromatography, or other standard techniques) with profiles of OMP extracts derived from cells grown in media containing standard amounts of iron and no iron-scavenging agents.

A composition "enriched in iron-regulated proteins" is one having an increased concentration of one or more of these proteins when compared to the concentration of such protein or. proteins in the composition derived from cultures grown under normal, non-iron-restricted growth conditions. A composition can be enriched in the protein or proteins by adding additional amounts of one or more of the proteins to the composition and/or by altering the media and/or growth conditions to increase production of the protein or proteins.

The term "leukotoxin" intends a protein belonging to the family of molecules characterized by a series of repeated amino acid domains near the carboxy terminus. The consensus amino acid sequence is Gly-Gly-X-Gly-X-Asp (SEQ ID NO:4) (Highlander et al., DNA (1989) 8:15–28), where X is Lys, Asp, Val or Asn. Such proteins include, among others, leukotoxins derived from *P. haemolytica* and *Actinobacillus pleuropneumoniae*, as well as *E. coli* alpha hemolysin (Strathdee, C. A., and Lo, R. Y. C. *Infect. Immun.* (1987) 55:3233–3236; Lo, R. Y. C., *Can. J. Vet. Res.* (1990) 54:S33–S35; Welch, R. A., *Mol. Microbiol.* (1991) 5:521–528). This family of toxins is known as the "RTX" family of toxins (Lo, R. Y. C., *Can. J. Vet. Res.* (1990) 54:S33–S35). The desired leukotoxin may be chemically synthesized, isolated from an organism expressing the same, or recombinantly produced. Furthermore, the term intends an immunogenic protein having an amino acid sequence substantially homologous to a contiguous amino acid sequence found in the particular native leukotoxin molecule. Thus, the term includes both full-length and partial sequences, as well as analogs. Although native full-length leukotoxins display leukotoxic activity, the term "leukotoxin" also intends molecules which remain immunogenic yet lack the cytotoxic character of native leukotoxins. The nucleotide sequences and corresponding amino acid sequences for several leukotoxins are known. See, e.g., U.S. Pat. Nos. 4,957,739 and 5,055,400; Lo et al., *Infect. Immun.* (1985) 50:667–67; Lo et al., *Infect. Immun.* (1987) 55:1987–1996; Strathdee, C. A., and Lo, R. Y. C., *Infect. Immun.* (1987) 55:3233–3236; Highlander et al., DNA (1989) 8:15–28; Welch, R. A., *Mol. Microbiol.* (1991) 5:521–528.

Figure 4:
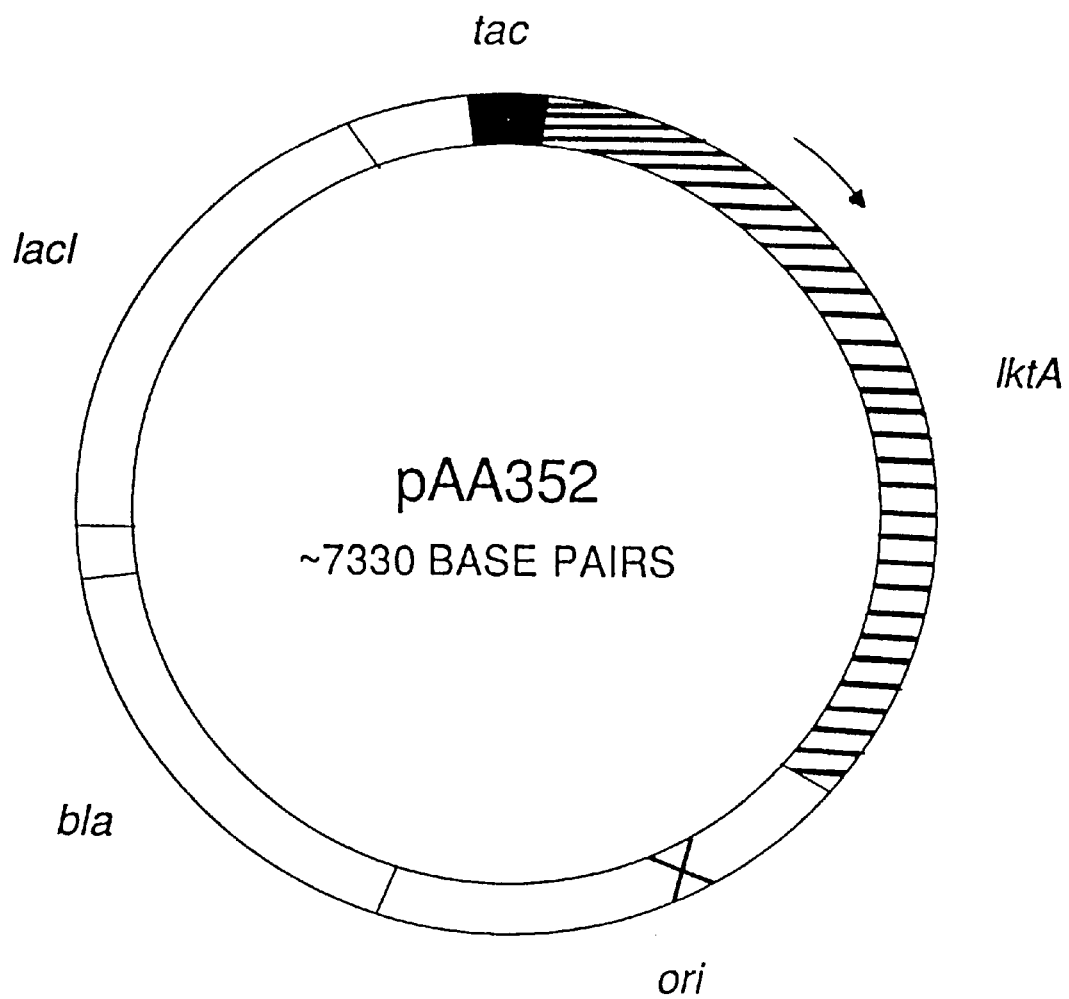
FIG. 4 depicts the structure of Plasmid pAA352 wherein tac is the hybrid trp::lac promoter from *E. coli*; bla represents the beta lactamase gene (ampicillin resistance); ori is the ColEl-based plasmid origin of replication; lktA is the *P. haemolytica* leukotoxin structural gene; and lacI is the *E. coli* lac operon repressor. The direction of transcription/translation of the leukotoxin gene is indicated by the arrow. The size of each component is not drawn to scale.

By "LKT 352" is meant a protein which is derived from the 1ktA gene present in plasmid pAA352 (FIG. 4, ATCC Accession No. 68283). The nucleotide sequence and corresponding amino acid sequence of this gene are described in International Publication No. WO91/15237 and shown in FIG. 5 (FIGS. 5A through 5F (SEQ ID NOS:1–2). The gene encodes a truncated leukotoxin, having 931 amino acids, which lacks the cytotoxic portion of the molecule. The derived LKT 352 is not necessarily physically derived from the sequence present in plasmid pAA352. Rather, it may be generated in any manner, including for example, by chemical synthesis or recombinant production. In addition, the amino acid sequence of the protein need only be substantially homologous to the depicted sequence. Thus, sequence variations may be present so long as the protein is immunogenic and lacks the cytotoxic attributes of full-length leukotoxin.

Two polypeptide sequences are "substantially homologous" when at least about 80% (preferably at least about 90%, and most preferably at least about 95%) of the amino acids match over a defined length of the molecule. As used herein, substantially homologous also refers to sequences showing identity to the specified polypeptide sequence.

The term "functionally equivalent" intends that the amino acid sequence of the subject polypeptide is one that will elicit an immunological response, as defined below, equivalent to an immunogenic leukotoxin polypeptide.

An "isolated" protein is a protein separate and discrete from a whole organism (live or killed) with which the protein is normally associated in nature. Thus, a protein contained in a cell free extract would constitute an "isolated" protein, as would a protein synthetically or recombinantly produced.

An "antigen" refers to a molecule containing one or more epitopes that will stimulate a host's immune system to make a humoral and/or cellular antigen-specific response. The term is also used interchangeably with "immunogen." A "subunit antigen," like an isolated protein, refers to an antigen entity separate and discrete from a whole organism (live or killed) with which the antigen is associated in nature and is not meant to denote the method by which the antigen is obtained.

The term "epitope" refers to the site on an antigen or hapten to which specific B cells and T cells respond. The term is also used interchangeably with "antigenic determinant" or "antigenic determinant site." One such epitope is the consensus sequence found among a variety of leukotoxins, as described above. This sequence is Gly-Gly-X-Gly-X-Asp (SEQ ID NO:4), where X is preferably Lys, Asp, Val or Asn. Other substitutions for X in the consensus sequence are also contemplated including substitutions with an aliphatic amino acid, such as Gly, Ala, Val, Leu, Ile, a charged amino acid such as Asp, Glu, Arg, His or Lys, or a corresponding neutral amino acid such as Asn or Gln.

An "immunological response" to a composition or vaccine is the development in the host of a cellular and/or antibody-mediated immune response to the composition or vaccine of interest. Usually, such a response includes but is not limited to one or more of the following effects; the production of antibodies, B cells, helper T cells, suppressor T cells, and/or cytotoxic T cells and/or $_{\gamma}\delta$ T cells, directed specifically to an antigen or antigens included in the composition or vaccine of interest.

The terms "immunogenic" protein, polypeptide or amino acid sequence refer to an amino acid sequence which elicits an immunological response as described above. An "immunogenic" protein, polypeptide or amino acid sequence, as used herein, includes the full-length (or near full-length) sequence of the protein in question, analogs thereof, or immunogenic fragments thereof. By "immunogenic fragment" is meant a fragment of a polypeptide which includes one or more epitopes and thus elicits the immunological response described above. Such fragments will usually be at least about 2 amino acids in length, more preferably about 5 amino acids in length, and most preferably at least about 10 to 15 amino acids in length. There is no critical upper limit to the length of the fragment, which could comprise nearly the full-length of the protein sequence, or even a fusion protein comprising two or more epitopes of the protein.

By "vertebrate subject" is meant any member of the subphylum chordata, including mammals such as cattle, sheep, pigs, goats, horses, as well as birds. The term does not denote a particular age. Thus, both adult and newborn animals are intended to be covered.

The terms "polypeptide" and "protein" are used interchangeably and in their broadest sense, i.e., any polymer of amino acids (dipeptide or greater) linked through peptide bonds. Thus, the term "polypeptide" includes proteins (having both the full-length sequence or fragments thereof), oligopeptides, analogs, muteins, fusion proteins and the like.

"Native" proteins or polypeptides refer to proteins or polypeptides having an amino acid sequence equivalent to a protein recovered from a source occurring in nature. Thus, the term "native leukotoxin" would include a protein with the same amino acid sequence as a naturally occurring leukotoxin, and fragments thereof. "Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A composition containing A is "substantially free of" B when at least about 85% by weight of the total of A+B in the composition is A. Preferably, A comprises at least about 90% by weight of the total of A+B in the composition, more preferably at least about 95%, or even 99% by weight.

The term "treatment" as used herein refers to either (i) the prevention of infection or reinfection (prophylaxis), or (ii) the reduction or elimination of symptoms of the disease of interest (therapy).

B. General Methods

Central to the instant invention is the discovery that *H. somnus* OMP preparations enriched in iron-regulated proteins, provide protection against *H. somnus* related diseases. Such enriched vaccines contain antigens which are not present under normal growth conditions and, therefore, include additional components which afford protection against *H. somnus* infection. The *H. somnus* OMP extract can be used either alone or in combination with a leukotoxin, preferably a *P. haemolytica* derived leukotoxin, and/or saline extracts of *P. haemolytica*, in vaccine compositions to protect animals against *H. somnus* infections and respiratory diseases such as pneumonia, including shipping fever pneumonia. Such *H. somnus* infections include thromboembolic meningoencephalitis (ITEME), septicemia, arthritis, and pneumonia (Corbelll, L. B., *Can. J. Vet. Res.* (1990) 54:S57–S62; Harris, F. W., and Janzen, E. D., *Can. Vet. J.* (1990) 30:816–822; Humphrey, J. D., and Stephens, L. R., *Vet. Bull.* (1983) 53:987–1004), as well as myocarditis, pericarditis, spontaneous abortion, infertility and mastitis.

*H. somnus* OMP extracts are conveniently enriched in iron-regulated proteins by manipulating the media and growth conditions to assure expression of the same. This can be accomplished by culturing *H. somnus* in an iron-restricted environment. (Since *H. somnus* is now believed to be the same organism as those previously identifed as *Histophilus ovis* and *Haemophilus agni* (Philbey et al., *Aust. Vet. J.* (1991) 88:387–390), iron-enriched OMP extracts from these organisms are also intended to be covered by the present invention.)

Media lacking in iron can be easily formulated. For example, iron can be removed from standard growth media by passing the media over e.g. an ion-exchange resin. Alternatively, media can be formulated which lacks iron but includes other nutrients essential for growth. A particularly preferred method of achieving iron restriction is by adding a nontoxic chelating agent capable of scavenging iron to the media at an appropriate time during culturing. For example, the addition of about 50 to 500 μM dipyridyl, preferably about 80 μM dipyridyl, to the cell culture media, will create an iron-restricted environment sufficient to assure the expression of iron-regulated proteins. Similarly, the addition of about 20 to 100 μM deferrated EDDA (Rogers, H. J., *Infect. Immun.* (1973) 7:445–456), will also suffice (see, Lee, B. C., *Infect. Immun.* (1992) 60:810–816; Pidcock et al., *Infect. Immun.* (1988) 56:721–725). Other concentrations and chelating agents can also be used and will be readily identifiable to those of skill in the art. For example, iron-chelators such as, but not limited to, transferrin, lactoferrin, desferol, conalbumin, protoporphyrin 9, as well as most siderophores, will find use in the present invention. The chelating agent(s) is preferably added during mid-log phase to assure optimal cell growth yet adequate expression of the iron-regulated proteins.

OMPs can be extracted from the *H. somnus* cultures using a variety of methods. For example, following growth in iron-restricted media, cells can be disrupted by mechanical means (i.e. using glass beads and the like), freeze-thawing, sonicating, detergent solubilization (i.e. with Triton or a similar detergent which does not significantly denature the extracted OMP antigens) or by using a combination of all of the above (see, e.g. Schnaitman, C. A., *J. Bacteriol.* (1971) 108:545–563; Theisen, M. and Potter, A., *J. Bacteriol.* (1992) 174:17–23; U.S. Pat. Nos. 4,877,613 and 4,981,685). Soluble proteins can be separated from insoluble proteins and detergent and other unwanted substances removed using standard techniques, such as centrifugation and/or dialysis. Alternative methods for obtaining OMP extracts are known in the art. Suitable pharmaceutical vehicles and/or adjuvants (described below) can then be added to the iron-enriched OMP extracts and the vaccine compositions administered to animals to be immunized.

Prior to immunization, one or more leukotoxins can be added to the *H. somnus* extract in order to provide additional protection against respiratory diseases such as shipping fever pneumonia. In this way, a single vaccine can protect against a multitude of diseases which commonly affect livestock and other economically important farm animals.

As explained above, leukotoxin contemplated for use in the instant vaccines includes any leukotoxin derived from the RTX family of molecules. It is to be understood that modifications of the native amino acid sequence of these leukotoxins which result in proteins which have substantially equivalent or enhanced activity as compared to the native sequences, are also contemplated. These modifications may be deliberate, as through site-directed mutagenesis, or may be accidental, such as through mutation of hosts which produce the leukotoxins. All of these modifications are included, so long as immunogenic activity is retained.

Additionally, both full-length leukotoxin, immunogenic fragments thereof, and fusion proteins comprising the same, are intended for use in the subject vaccines. The sequence of the various full-length RTX leukotoxins are known and have been described (see, e.g., U.S. Pat. Nos. 4,957,739 and 5,055,400; Lo et al., *Infect. Immun.* (1985) 50:667–67; Lo et al., *Infect. Immun.* (1987) 55:1987–1996; Strathdee, C. A., and Lo, R. Y. C., *Infect. Immun.* (1987) 55:3233–3236; Highlander et al., DNA (1989) 8:15–28; Welch, R. A., *Mol. Microbiol.* (1991) 5:521–528.

Particularly useful in the subject vaccines are leukotoxins derived from *P. haemolytica*. Such leukotoxins include both full-length and truncated forms of the molecule which eliminate the cytotoxic activity thereof. A particularly preferred leukotoxin for use in the present vaccines is a truncated leukotoxin termed "LKT 352" which is defined above. The sequence of LKT 352 is depicted in FIGS. 5A through 5F (SEQ ID NOS:1–2) and the cloning strategy is described in the examples herein as well as in International Publication No. WO91/15237. Also of use is a leukotoxin:B-galactosidase fusion protein produced from plasmid pAA101 (ATCC Accession No. 67883) described below in the examples and in International Publication No. WO91/15237.

Epitopes of the above leukotoxins can also be used in combination with the *H. somnus* OMP extracts. An example of one such epitope is a polypeptide containing the consensus amino acid sequence, Gly-Gly-X-Gly-X-Asp (SEQ ID NO:4), described above. Epitope-containing polypeptides will generally include at least 4–30 amino acids. Smaller fragments encompassing the epitope may be inserted into larger peptides or polypeptides, such that the regions flanking the epitope are not those that are encoded within the naturally occurring genes. The techniques for the synthesis of these peptides or polypeptides are apparent to one of average skill in the art. For example, the genetic sequence encoding a particular antigen may be isolated via cloning, and that sequence altered at sites other than that encoding the particular epitope. This alteration may be accomplished by site specific mutation, or by deletions, or by insertions. Alternatively, an oligonucleotide sequence encoding the epitope may be inserted into or attached to another sequence which encodes a different peptide or polypeptide. A recombinant sequence is then inserted into an expression vector which is compatible with the host to be transformed, and the expression system used to synthesize the desired peptide which includes the particular epitope. The techniques by which this may be accomplished are known to those of skill in the art. See, e.g., T. Maniatis et al., supra; *DNA Cloning*, Vols. I and II, supra; and *Nucleic Acid Hybridization*, supra. Alternatively, an oligopeptide may be synthesized by solid phase synthesis which includes the particular epitope, but which adds flanking amino acids to it which are not in the sequence of the naturally occurring antigen.

The above leukotoxins can be produced recombinantly using techniques well known in the art. Cloning strategies for leukotoxins are generally known and described herein as well as in, e.g., U.S. Pat. Nos. 4,957,739 and 5,055,400; International Publication No. WO91/15237; Lo et al., *Infect. Immun.* (1985) 50:667–67; Lo et al., *Infect. Immun.* (1987) 55:1987–1996; Strathdee, C. A., and Lo, R. Y. C., *Infect. Immun.* (1987) 55:3233–3236; Highlander et al., DNA (1989) 8:15–28; and Welch, R. A., *Mol. Microbiol.* (1991) 5:521–528.

The leukotoxin can also be purified from native bacteria using standard protein purification procedures. See, e.g., *Protein Purification Principles and Practice* 2d edition (Robert K. Scopes ed. 1987). Such techniques include gel filtration chromatography, ion exchange chromatography, affinity chromatography, immunoadsorbent chromatography, polyacrylamide gel electrophoresis and other electrophoretic techniques, centrifugation, dialysis, and precipitation.

The leukotoxin and epitopes thereof for use in the present invention may also be produced by chemical synthesis such as solid phase peptide synthesis, using known amino acid sequences or amino acid sequences derived from the DNA sequence of the gene of interest. Such methods are known to those skilled in the art. Chemical synthesis is particularly convenient for the production of small immunogenic fragments of the leukotoxin.

Saline extracts of *P. haemolytica* can also be combined with any of the above subunit antigens. These extracts are produced by extracting proteins in an 0.85% (w/v) sodium chloride solution. The extract can be further treated, i.e. with glass beads and agitation, or other methods known in the art, to remove cell surface proteins. The combination of such saline extracts with the *H. somnus* OMP preparations, with or without isolated or recombinantly produced leukotoxin, affords additional protection against shipping fever.

Vaccine Formulations and Administration

Animals can be immunized with the compositions of the present invention by administration of the same via any of several methods, described below. Prior to immunization, it may be desirable to increase the immunogenicity of the particular protein, or an analog of the protein, or particularly fragments of the protein. This can be accomplished in any one of several ways known to those of skill in the art. For example, the antigenic peptide may be administered linked to a carrier. For example, a fragment may be conjugated with a macromolecular carrier. Suitable carriers are typically large, slowly metabolized macromolecules such as: proteins; polysaccharides, such as sepharose, agarose, cellulose, cellulose beads and the like; polymeric amino acids such as polyglutamic acid, polylysine, and the like; amino acid copolymers; and inactive virus particles. Especially useful protein substrates are serum albumins, keyhole limpet hemocyanin, immunoglobulin molecules, thyroglobulin, ovalbumin, and other proteins well known to those skilled in the art.

The protein substrates may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

The novel proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK⁻ recombinant can be selected by culturing the cells in the presence of 5-bromodeoxyuridine and picking viral plaques resistant thereto.

It is also possible to immunize a subject with a protein of the present invention, or a protective fragment thereof, or an analog thereof, which is administered alone, or mixed with a pharmaceutically acceptable vehicle or excipient. Typically, vaccines are prepared as injectables, either as liquid solutions or suspensions; solid forms suitable for solution in, or suspension in, liquid vehicles prior to injection may also be prepared. The preparation may also be emulsified or the active ingredient encapsulated in liposome vehicles. The active immunogenic ingredient is often mixed with vehicles containing excipients which are pharmaceutically acceptable and compatible with the active ingredient. Suitable vehicles are, for example, water, saline, dextrose, glycerol, ethanol, or the like, and combinations thereof. In addition, if desired, the vehicle may contain minor amounts of auxiliary substances such as wetting or emulsifying agents, pH buffering agents, or adjuvants which enhance the effectiveness of the vaccine. Adjuvants may include for example, muramyl dipeptides, avridine, aluminum hydroxide, oils, saponins and other substances known in the art. Actual methods of preparing such dosage forms are known, or will be apparent, to those skilled in the art. See, e.g., Remington's Pharmaceutical Sciences, Mack Publishing Company, Easton, Pa., 15th edition, 1975. The composition or formulation to be administered will, in any event, contain a quantity of the protein adequate to achieve the desired immunized state in the individual being treated.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The proteins can also be delivered using implanted mini-pumps, well known in the art.

Furthermore, the proteins (or complexes thereof) may be formulated into vaccine compositions in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

To immunize a vertebrate subject, the polypeptide of interest is generally administered parenterally, usually by intramuscular injection, in an appropriate vehicle. Other modes of administration, however, such as subcutaneous, intravenous injection and intranasal delivery, are also acceptable. Injectable vaccine formulations will contain an effective amount of the active ingredient in a vehicle, the exact amount being readily determined by one skilled in the art. The active ingredient may typically range from about 1% to about 95% (w/w) of the composition, or even higher or lower if appropriate. The quantity to be administered depends on the animal to be treated, the capacity of the animal's immune system to synthesize antibodies, and the degree of protection desired. With the present vaccine formulations, 0.1 mg of active ingredient per ml of injected solution should be adequate to raise an immunological response when a dose of 1 to 2 ml per animal is administered. Other effective dosages can be readily established by one of ordinary skill in the art through routine trials establishing dose response curves.

The subject is immunized by administration of the particular antigen or fragment thereof, or analog thereof, in at least one dose, and preferably two doses. Moreover, the animal may be administered as many doses as is required to maintain a state of immunity to *H. somnus* infection.

An alternative route of administration involves gene therapy or nucleic acid immunization. Thus, nucleotide sequences (and accompanying regulatory elements) encoding the subject proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see, International Publication No. WO90/11092; and Wolff et al., *Science* (1990) 247:1465–1468). Liposome-mediated gene transfer can also be accomplished using known methods. See, e.g., Hazinski et al., *Am. J. Respir. Cell Mol. Biol.* (1991) 4:206–209; Brigham et al., *Am. J. Med. Sci.* (1989) 298:278–281; Canonico et al., *Clin. Res.* (1991) 39:219A; and Nabel et al., *Science* (1990) 249:1285–1288. Targeting agents, such as antibodies directed against surface antigens expressed on specific cell types, can be covalently conjugated to the liposomal surface so that the nucleic acid can be delivered to specific tissues and cells susceptible to *H. somnus* infection.

Below are examples of specific embodiments for carrying out the present invention. The examples are offered for illustrative purposes only, and are not intended to limit the scope of the present invention in any way.

Deposits of Strains Useful in Practicing the Invention

A deposit of biologically pure cultures of the following strains was made with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description.

| Strain | Deposit Date | ATCC No. |
| --- | --- | --- |
| *P. haemolytica* serotype 1 B122 | February 1, 1989 | 53863 |
| pAA101 in *E. coli* JM105 | February 1, 1989 | 67883 |
| pAA352 in *E. coli* W1485 | March 30, 1990 | 68283 |

C. Experimental

Materials and Methods

Enzymes were purchased from commercial sources, and used according to the manufacturers' directions. Radionucleotides and nitrocellulose filters were also purchased from commercial sources.

In the cloning of DNA fragments, except where noted, all DNA manipulations were done according to standard procedures. See, T. Maniatis et al., supra. Restriction enzymes, $T_4$ DNA ligase, *E. coli*, DNA polymerase I, Klenow fragment, and other biological reagents were purchased from commercial suppliers and used according to the manufacturers' directions. Double-stranded DNA fragments were separated on agarose gels.

cDNA and genomic libraries were prepared by standard techniques in pUC13 and the bacteriophage lambda gt11, respectively. See, DNA CLONING: Vols I and II, supra.

*P. haemolytica* biotype A, serotype 1 ("A1") strain B122 was isolated from the lung of a calf which died of pneumonic pasteurellosis and was stored at −70° C. in defibrinated blood. Routine propagation was carried out on blood agar plates or in brain heart infusion broth (Difco Laboratories, Detroit, Mich.) supplemented with 5% (v/v) horse serum (Gibco Canada Ltd., Burlington, Canada). All cultures were incubated at 37° C.

*Haemophilus somnus* (Strain HS25) was isolated from the lung of a calf which died of acute pneumonia. Cultures were obtained from the Alberta Department of Agriculture and were maintained at −70° C. One of these cultures was passaged on Brain Heart Infusion Agar supplemented with 10 mM Tris-HCl, pH8 and thiamine monophosphate (2 μg/ml) (BHITT agar) and administered to a calf intravenously. Synovial fluid was collected and stored at −70° C. A representative sample was sent to the Diagnostic Bacteriology Laboratory at the Department of Veterinary Microbiology (Western College of Veterinary Medicine) for identification and was confirmed to be *H. somnus*.

A working stock of *H. somnus* HS25 was derived as follows. A blood agar plate was streaked with strain HS25 and incubated at 37° C. overnight in a $CO_2$ (5%) incubator. Ten to fifteen colonies were removed and inoculated into a flask containing 100 ml of 100% fetal bovine serum. This flask was incubated at 37° C. with gentle agitation (150 RPM) until the absorbance at 660 nm equalled 0.4–0.6 (≈5 hours). 1.5 ml volumes were then aliquoted into sterile Nunc vials (total of 48 vials) and placed in a plastic Nalgene holder. This container was stored under liquid nitrogen and these frozen vials were used in further experiments.

*H. somnus* strain HS25 has been used in challenge experiments to induce experimental Haemophilosis in calves (Harland, R. J., et al. *Conf. Res. Work. Anim. Dis.* 71st (1990) 29:6). Growth conditions for strain HS25 have been described (Theisen, M., and Potter, A. A. *J. Bacteriol.* (1992) 174:17–23).

EXAMPLE 1

The protective capacity of various *P. haemolytica* leukotoxins were tested by administering the recombinant and/or native products listed in Table 1 to calves.

TABLE 1

Proteins Administered To Calves In Example 1

(1) Control group—avridine (adjuvant) only.
(2) Authentic leukotoxin.
(3) Recombinant leukotoxin:B-galactosidase (from pAA101 described below).
(4) Recombinant leukotoxin (from pAA352 described below).
(5) Saline-extract of *P. haemolytica*.
(6) Saline-extract plus authentic leukotoxin.
(7) Saline-extract plus recombinant leukotoxin (from pAA352).

The products from Table 1 were made as follows.

Purification of *P. haemolytica* Native Leukotoxin

*P. haemolytica* A1 was grown to mid-log phase in Brain Heart Infusion broth (Difco) at 37° C. Cells were harvested by centrifuging at 9,000 rpm for 20 minutes using a Sorval GSA rotor. The supernatant was transferred to a fresh flask and ammonium sulfate added to 70% saturation. The mixture was stirred overnight in the cold. The precipitate was collected by centrifugation as above and the pellet was dissolved in 10 ml sterile water per liter of the original culture. The dissolved pellet was desalted by passage through Sephadex G-25. The collected sample was subjected to preparative isoelectric focusing using a rotofor apparatus (Biorad Labs) over a pH gradient of 5 to 7. Fractions over a range of pH 6–7 were pooled and NaCl added to 1.0 M. The sample was passed through a Sephadex G-25 column. The purified leukotoxin was loaded on a 12.5% SDS-polyacrylamide gel and the sample contained one major protein band corresponding to a molecular weight of 95,000.

1. Production of *P. haemolytica* Recombinant Leukotoxin from pAA101

To produce recombinant leukotoxin, gene libraries of *P. haemolytica* A1 (strain B122) were constructed using standard techniques. See, Lo et al., Infect. Immun., supra; DNA CLONING: Vols. I and II, supra; and T. MANIATIS et al., supra. A genomic library was constructed in the plasmid vector pUC13 and a DNA library constructed in the bacteriophage lambda gt11. The resulting clones were used to transform *E. coli* and individual colonies were pooled and screened for reaction with serum from a calf which had survived a *P. haemolytica* infection and that had been boosted with a concentrated culture supernatant of *P. haemolytica* to increase anti-leukotoxin antibody levels. Positive colonies were screened for their ability to produce leukotoxin by incubating cell lysates with bovine neutrophils and subsequently measuring release of lactate dehydrogenase from the latter.

Several positive colonies were identified and these recombinants were analyzed by restriction endonuclease mapping. One clone appeared to be identical to a leukotoxin gene cloned previously. See, Lo et al., *Infect. Immun.*, supra. To confirm this, smaller fragments were recloned and the restriction maps compared. It was determined that approximately 4 kilobase pairs of DNA had been cloned. Progressively larger clones were isolated by carrying out a chromosome walk (5' to 3' direction) in order to isolate full length recombinants which were approximately 8 kb in length. The final construct was termed pAA114. This construct contained the entire leukotoxin gene sequence. The structure of this plasmid is shown in FIG. 1.

Both full length and truncated versions of the leukotoxin gene were expressed. The truncated forms were fusions with B-galactosidase (lacZ). The full length versions were expressed using the native *P. haemolytica* promoter or the protein A gene (spa) promoter and signal sequence. Clones were constructed as follows.

Plasmids pLTX1.1 and pLTX3.2 were isolated from *P. haemolytica* genomic DNA as purified restriction fragments (1.0 kb and 2.1 kb, respectively) from an EcoRV Pst1 double digest. These fragments were cloned into pTZ18R digested with HincII Pst1. The vector was used to transform *E. coli* strain JM105. Transformed cells were identified by plating on media containing ampicillin plus Xgal and IPTG. Blue colonies indicated the presence of a functional lacZ gene. The DNA from these colonies was analyzed by restriction endonuclease digestion and found to contain the 5' end of the leukotoxin gene (lktC+lktA). This plasmid was termed pLTX3P.1.

Plasmid pLTX3P.1 was mutagenized in vitro with hydroxylamine, transformed into JM105 and plated on a growth medium containing ampicillin plus a reduced concentration of Xgal. In this way clones expressing increased quantities of the lktA:lacZ product would be dark blue whereas those containing an unmodified gene would be white or light blue. The clones from the dark blue colonies were termed pAA134.

Figure 2:
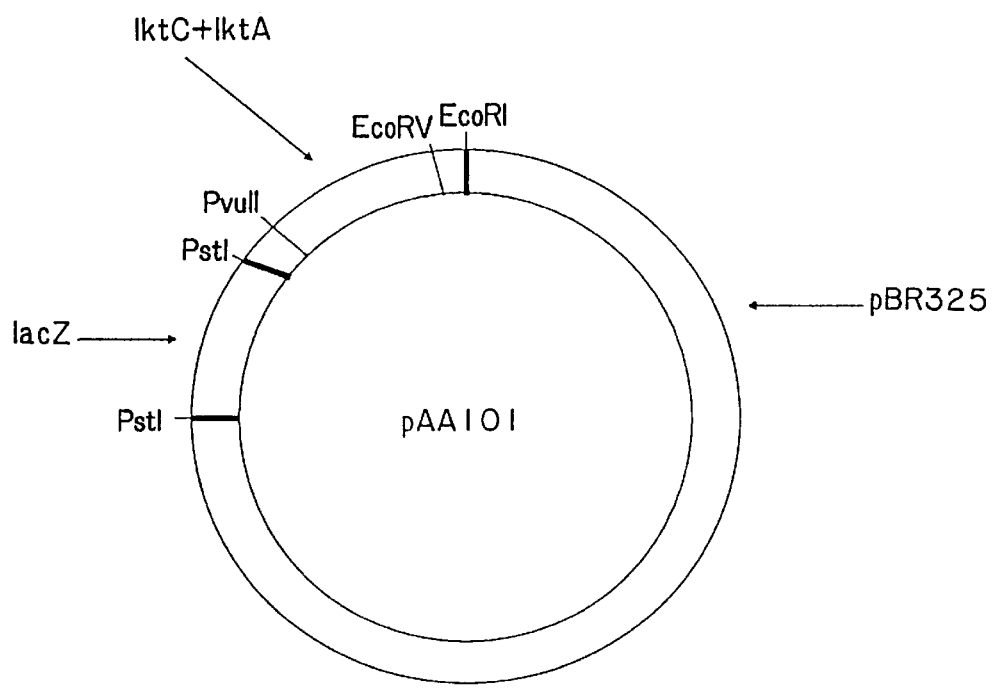
FIG. 2 depicts the structure of Plasmid pAA101.

A leukotoxin EcoRV/Pstl 5'-fragment (from pLTX3P.1) was subcloned into pBR325 digested with EcoRl/Pstl containing the native leukotoxin promoter (from pLTX3P.1), plus a promoterless full length lacZ gene from plasmid pMC1871 (Pst1 fragment). The plasmid was used to transform *E. coli* JM105 and blue colonies were isolated from Xgal agar. This plasmid was termed pAA101 and is illustrated in FIG. 2. The predicted amino acid sequence of the fusion protein is shown in FIG. 3 (SEQ ID NO:3).

2. Production of *P. haemolytica* Recombinant Leukotoxin from pAA352

A second version of recombinant *P. haemolytica* leukotoxin was expressed. This leukotoxin was termed "leukotoxin 352" or "LKT 352". In order to produce this leukotoxin, the following gene construct was prepared from pAA114 described above.

lktA, a MaeI restriction endonuclease fragment which contained the entire gene was treated with the Klenow fragment of DNA polymerase I plus nucleotide triphosphates and ligated into the SmaI site of the cloning vector pUC13. This plasmid was named pAA179. From this, two expression constructs were made in the ptac-based vector pGH432: lacI digested with SmaI. One, pAA342, consisted of the 5'-AhaIII fragment of the lktA gene while the other, pAA345, contained the entire MaeI fragment described above. The clone pAA342 expressed a truncated leukotoxin peptide at high levels while pAA345 expressed full length leukotoxin at very low levels. Therefore, the 3' end of the lktA gene (StyI BamHI fragment from pAA345) was ligated to StyI BamHI-digested pAA342, yielding the plasmid pAA352. The structure of this plasmid is shown in FIG. 4.

The nucleotide sequence of the leukotoxin expressed by plasmid pAA352 (LKT 352 or new leukotoxin) is shown in FIGS. 5A through 5F (SEQ ID NOS:1–2). The peptide encoded by this sequence is 931 amino acids in length and is 98% homologous to authentic leukotoxin. This recombinant leukotoxin migrates, on polyacrylamide gels, to a position identical to authentic leukotoxin.

3.a. Purification of Recombinant Leukotoxin from Example 1.1

Two liters of *E. coli* JM105/pAA101 were grown in broth to mid-exponential growth phase and the cells harvested by centrifugation. The pellet was resuspended in 50 ml of TEP buffer (100 mM Tris-HCl, pH 7.4, 10 mM EDTA, 1 mM phenyl methyl sulfonyl fluoride), immediately frozen at −70° C. and held overnight. The cells were then thawed and sonicated for a total of 4 minutes (30 second bursts, 200 W) and the cell debris removed by centrifugation at 10,000 rpm in a Sorvall SS-34 rotor. The supernatant was mixed with three volumes of saturated ammonium sulfate and stirred at 4° C. for 60 minutes. This slurry was stored at 4° C. overnight then centrifuged as above. The pellet obtained from *E. coli* JM105/pAA101 cells was dissolved in 10 ml of TEP buffer and diluted to 20 ml with TBSN (10 mM Tris-HCl, pH 8, 500 mM NaCl, 0.2% NP-40). This solution was passed through an affinity column containing a monoclonal antibody to B-galactosidase ("Protosorb" from Promega Biotech). The column was washed once with 20 ml TBSN. The fusion protein was eluted with 5.0 ml of 0.1 M NaHCO$_3$/Na$_2$CO$_3$, pH 10.8, and stored at 4° C.

3.b. Purification of Recombinant Leukotoxin (LKT 352) from Example 1.2

Recombinant LKT 352 was purified using the following procedure. Five to ten colonies of *E. coli* W1485/pAA352 (ATCC no. 68283) were inoculated into 10 ml of TB broth supplemented with 100 micrograms/ml of ampicillin and incubated at 37° C. for 6 hours on a G10 shaker, 220 rpm. Four ml of this culture was diluted into each of two baffled Fernbach flasks containing 400 ml of TB broth +ampicillin and incubated overnight as described above. Cells were harvested by centrifugation for 10 minutes at 4,000 rpm in polypropylene bottles, 500 ml volume, using a Sorvall GS3 rotor. The pellet was resuspended in an equal volume of TB broth containing ampicillin which had been prewarmed to 37° C. (i.e., 2×400 ml), and the cells were incubated for 2 hours as described above.

3.2 ml of isopropyl-B,D-thiogalactopyranoside (IPTG, Gibco/BRL), 500 mM in water (final concentration=4 mM), was added to each culture in order to induce synthesis of recombinant leukotoxin. Cultures were incubated for two hours. Cells were harvested by centrifugation as described above, resuspended in 30 ml of 50 mM Tris-hydrochloride, 25% (w/v) sucrose, pH 8.0, and frozen at −70° C. The frozen cells were thawed at room temperature after 60 minutes at −70° C., and 5 ml of lysozyme (Sigma, 20 mg/ml in 250 mM Tris-HCl, pH 8.0) was added. The mixture was vortexed at high speed for 10 seconds and then placed on ice for 15 minutes. The cells were then added to 500 ml of lysis buffer in a 1000 ml beaker and mixed by stirring with a 2 ml pipette. The beaker containing the lysed cell suspension was placed on ice and sonicated for a total of 2.5 minutes (5–30 second bursts with 1 minute cooling between each) with a Braun sonicator, large probe, set at 100 watts power. Equal volumes of the solution were placed in Teflon SS34 centrifuge tubes and centrifuged for 20 minutes at 10,000 rpm in a Sorvall SS34 rotor. The pellets were resuspended in a total of 100 ml of sterile double distilled water by vortexing at high speed, and the centrifugation step repeated. Supernatants were discarded and the pellets combined in 20 ml of 10 mM Tris-HCl, 150 mM NaCl, pH 8.0 (Tris-buffered saline) and the suspension frozen overnight at −20° C.

The recombinant leukotoxin suspension was thawed at room temperature and added to 100 ml of 8 M Guanidine HCl (Sigma) in Tris-buffered saline and mixed vigorously. A magnetic stir bar was placed in the bottle and the solubilized sample was mixed at room temperature for 30 minutes. The solution was transferred to a 2000 ml Ehrlenmyer flask and 1200 ml of Tris-buffered saline was quickly added. This mixture was stirred at room temperature for an additional 2 hours. 500 ml aliquots were placed in dialysis bags (Spectrum, 63.7 mm diameter, 6,000–8,000 MW cutoff, #132670, from Fisher scientific) and these were placed in 4,000 ml beakers containing 3,500 ml of Tris-buffered saline +0.5 M Guanidine HCl. The beakers were placed in a 4° C. room on a magnetic stirrer overnight after which dialysis buffer was replaced with Tris-buffered saline+0.1 M Guanidine HCl and dialysis continued for 12 hours. The buffer was then replaced with Tris-buffered saline +0.05 M Guanidine HCl and dialysis continued overnight. The buffer was replaced with Tris-buffered saline (no guanidine), and dialysis continued for 12 hours. This was repeated three more times. The final leukotoxin solution was poured into a 2000 ml plastic roller bottle (Corning) and 13 ml of 100 mM PMSF (in ethanol) was added to inhibit protease activity. The solution was stored at −20° C. in 100 ml aliquots.

Preparation of *P. haemolytica* Saline Extract For Use in Vaccination Trial A

A one liter culture of *P. haemolytica* A1 (strain B122) was prepared in Brain Heart Infusion Broth (Difco) and the cells were harvested by centrifugation at 9,000 rpm for 20 minutes with a Sorvall GSA rotor. The pellet was washed once with 200 ml of 0.85% sodium chloride (w/v) which had been preheated to 65° C. and resuspended in 30 ml of the saline solution. The suspension was heated to 65° C. for 20 minutes with continuous stirring and the bacteria removed by centrifugation. The supernatant was decanted and stored at 4° C.

Preparation of *P. haemolytica* Saline Extract for Use in Vaccination Trial D

A saline extract was made as above with the following modifications. Cells were harvested by centrifugation at 5,000 rpm for 10 minutes with a Sorvall GS3 rotor. After washing, the pellet was resuspended in 100 ml of the sodium chloride solution which had been preheated to 65° C. The suspension was placed in a large flask (preheated to 65° C.), the bottom of which was covered with glass beads. The flask with cells was agitated vigorously in a New Brunswick G25 shaker (250–300 rpm) at 65° C. for one hour. The sample was then centrifuged for 20 minutes at 10,000 rpm in a Sorvall SS34 rotor. The supernatant was carefully decanted into a sterile bottle. Phenylmethyl sulfonylfluoride was added to a final concentration of 0.1 mM and stored at 20° C.

Preparation of the Vaccine Compositions

Each dose of vaccine compositions listed in Table 1 above, were prepared by mixing 1.0 ml of the antigen listed (100 μg) 0.1 M PBS, pH 7.2, with an equal volume of freshly prepared avridine. Groups of six calves were vaccinated intramuscularly and boosted three weeks later with the same vaccine composition. 10 days after boosting, the calves were exposed to bovine herpes virus-1 followed by exposure to *P. haemolytica* A-1 strain B122 four days later. Calves were monitored for clinical signs of disease, temperature and weight loss. The results of this trial (vaccination Trial A) are shown in Table 2.

TABLE 2

Results of Vaccination Trial A of Example I

| Group | Antigen | Mortality (# of calves dead/6 calves) | Presence of Pasteurellosis Symptoms (+) | Mean Clinical Score per Day |
|---|---|---|---|---|
| 1 | Control (avridine only) | 5 | + | 10.7 |
| 2 | Authentic Leukotoxin | 1 | + | 4.0 |
| 3 | Recombinant Leukotoxin | 0 | − | 1.2 |
| 5 | Saline Extract | 1 | + | 2.6 |
| 6 | Saline Extract plus Authentic Leukotoxin | 0 | − | 1.1 |

As illustrated in Table 2, groups 3 and 6 were completely protected while groups 2 and 5 were significantly protected. The control group, group 1, had the highest mortality rate. These results indicate that the recombinant leukotoxin:B-galactosidase fusion protein, as well as authentic leukotoxin, are effective immunogens for the prevention of bovine pneumonic pasteurellosis. It is possible that the protection afforded by the saline extract is at least partially due to the presence of leukotoxin.

A second vaccination trial (Vaccination Trial B) was carried out using the purified recombinant leukotoxin fusion protein described above. This protein was mixed with emulsigen (25% v/v) and calves vaccinated according to the groups listed in Table 3. The calves were boosted after 3 weeks and finally challenged with bovine herpes virus/*P. haemolytica* as described above. The results of this trial can be seen in Table 3.

TABLE 3

Results of Vaccination Trial B of Example 1

| Group | Mortality |
|---|---|
| 1. Emulsigen only | 8/9 |
| 2. Emulsigen + 100 μg antigen | 4/10 |
| 3. Emulsigen + 50 μg antigen | 4/6 |
| 4. Emulsigen + 25 μg antigen | 5/6 |
| 5. Emulsigen + 12.5 μg antigen | 5/6 |

As can be seen, Groups 2 and 3, administered emulsigen plus 100 μg and 50 μg of antigen, respectively, demonstrated a lower mortality rate than the control group. It should be noted that this experiment was done with a less than optimum adjuvant, possibly accounting for the higher mortality rates over those seen in vaccination trial A.

The immunogenicity of recombinantly produced LKT 352, prepared as described above, was tested in a third vaccination trial (vaccination Trial C) as follows. Twelve beef-type calves were randomized into two groups of six. The control group was vaccinated with placebo comprised of sterile saline combined with adjuvant. The second group was vaccinated with 100 μg of LKT 352 in adjuvant. Two injections were given intramuscularly 21 days apart. Each calf was bled at the time of each vaccination and 12 days following the second vaccination. The anti-leukotoxin titers were determined by a standard ELISA and are shown in Table 4.

TABLE 4

Anti-Leukotoxin Titers of Calves Vaccinated with LKT 352

| Group | | Anti-Leukotoxin Titer at | | 10 Days After |
|---|---|---|---|---|
| | | First Vaccination | Second Vaccination | Second Vaccination |
| Controls | 057 | 250 | 970 | 600 |
| | 065 | 3,500 | 10,000 | 20,000 |
| | 073 | 1,000 | 1,200 | 1,000 |
| | 081 | 230 | 200 | 230 |
| | 089 | 600 | 430 | 980 |
| | 097 | 500 | 500 | 500 |
| Mean | | 1,013 | 2,216 | 3,885 |
| LKT | 352 | 2,500 | 150,000 | 100,000 |
| | 070 | 600 | 4,000 | 14,000 |
| | 078 | 1,900 | 18,000 | 25,000 |
| | 086 | 250 | 15,000 | 120,000 |
| | 094 | 700 | 1,100 | 130,000 |
| | 102 | 170 | 800 | 35,000 |
| Mean | | 1,020 | 33,133 | 70,667 |

As can be seen, anti-leukotoxin titers were significantly higher in the LKT 352-treated group than the control calves at the time of the second vaccination and 10 days following the second vaccination.

The protective capacity of recombinantly produced LKT 352 combined with a saline extract of *P. haemolytica* was tested in a fourth vaccination trial (Vaccination Trial D). LKT 352 and *P. haemolytica* saline extract (SE) were prepared using the general methods outlined above. The saline extract was found to have a protein concentration of 250 μg/ml. It was diluted with sterile double distilled water to a final volume of 1330 ml in order to adjust the protein concentration to 150 μg/ml. The recombinant LKT 352 contained 250 μg/ml of protein. Polyacrylamide gel electrophoresis revealed the presence of one major band and therefore, this antigen was used with no further dilution. Each dose of vaccine contained 100 μg of the new leukotoxin and 50 μg of saline extract.

Calves were vaccinated twice intramuscularly, 21 days apart with one of the following:

(1) Placebo; or (2) P. haenolytica subunit vaccine (LKT 352 plus SE) in Emulsigen Plus; or (3) *P. haemolytica* subunit vaccine in Avridine.

The experimental schedule was as follows:

| Day -31 | 1st vaccination |
|---|---|
| Day -10 | 2nd vaccination |

-continued

| | |
|---|---|
| Day 0 | Challenge with BHV-1 |
| Day 4 | Challenge with P. haemolytica |
| Day 5 | Clinical observation ends |

The results of this study can be seen in Table 5. As can be seen, twenty-five percent of the control calves died. In contrast, there was no mortality in the two groups given the subunit vaccine. The morbidity was also significantly lower in the subunit vaccine groups than in the placebo group (Fisher Exact Test p<0.05).

TABLE 5

Results of Vaccination Trial D

| Vaccine Group | n = | % Morbidity[a] | % Mortality[b] | Mean[c] Clinical Score | Mean[c] Temp (° C.) | Mean[d] Sick Days | Mean Wt[e] Change (kg) |
|---|---|---|---|---|---|---|---|
| 1. Placebo | 8 | 100% | 25% | 1.04 | 40.3 | 4.5 | −3.6 |
| 2. LKT 352 + SE in Emulsigen Plus | 8 | 50%* | 0% | 0.36 | 39.4 | 1 | +2.25 |
| 3. LKT 352 + SE in Avridine | 8 | 50%* | 0% | 0.44 | 39.5 | 1 | +3.75 |

[a]% of calves that developed a fever > 40.0 with clinical signs of BRD post P. haemolytica infection.
[b]% of calves that died of fibrinous pneumonia post P. haemolytica infection.
[c]Mean scores and temperatures of animals while alive.
[d]Mean days/calf that fever => 40.0 with clinical signs of BRD, calves that die are considered sick until end of trial.
[e]Mean change in weight (kg) from P. haemolytica infection until calf dies or trial ends.
*Morbidity was significantly lower (P < 0.05) than in the control group. Fisher's Exact Test.

A field trial (Vaccination Trial E) was carried out using the subunit vaccine comprised of LKT 352 and a P. haemolytica saline extract (SE). The vaccine formulations were as described in Vaccination Trial D.

The calves used were beef-type calves weighing from 250 kg to 325 kg. The calves were born during the spring, fall weaned, and purchased for the feedlot at auction markets. They were transported to the feedlot by truck and arrived within a few days of purchase.

Calves were randomly assigned to one of two vaccine groups. Calves in Group I were given a single 2 ml injection of the subunit Pasteurella vaccine intramuscularly. Calves in Group II were given a single 2 ml injection of placebo. The calves were processed at the time of arrival at the feedlot, and were assigned to one of the two treatment groups in rotation as they passed through a cattle chute. A technician administered the vaccines and recorded the treatment group to which each calf was assigned. A total of 2,324 calves were vaccinated, 1,168 in Group I and 1,156 in Group II.

Calves were kept and managed as typical feedlot animals. Feedlot cowboys were responsible for selecting and treating sick calves according to a protocol established by their consulting feedlot veterinarian. Selection of calves for treatment and post-mortem diagnosis was done without knowledge of the vaccination status of the calves. Records were maintained describing the daily diagnosis, temperature, and treatment of each sick calf. Calf health was monitored for 60 days after arrival. A gross post-mortem was done on all fatalities by a veterinarian within approximately 24 hrs of death and samples were submitted for further lab work if necessary. This information was used to establish morbidity (treatment) risks, and mortality risks. BRD morbidity risk scores were determined using the following equation:

$$BRD\ \text{Morbidity Risk} = \frac{\#\ \text{of calves sick with }BRD\text{ in Group}}{\#\ \text{of calves in Group initially}}$$

The statistical significance of the differences between groups was established using risk ratios (or relative risk, RR), and by determining the 95% confidence intervals using the Taylor series confidence intervals when the comparison was between 2 groups. Risk ratios were established using the following equation:

$$\text{Risk Ratio (Relative Risk, }RR\text{)} = \frac{\text{Risk for One Group}}{\text{Risk for the Comparison Group}}$$

The significance of the differences was determined using the Mantel-Haenszel technique for summary risk ratios (MHRR) and the Greenland and Robins technique for calculating the 95% confidence intervals. All RRs were considered statistically significant if 95% confidence intervals did not include unity. When RRs and confidence intervals could not be calculated, the Fisher Exact 2-tailed test was used to determine the statistical significance between risks.

The results of this trial can be seen in Table 6. As is apparent, vaccination with LKT 352 in combination with a P. haemolytica saline extract (Group I) significantly reduced bovine respiratory disease morbidity and bovine respiratory disease mortality (all pneumonias) as compared to treatment with the placebo (Group II). The reduction in fibrinous pneumonia mortality was not significant at the 5% level. However, this is probably because a bovine herpesvirus-1 vaccine was also tested in combination with the Pasteurella vaccine. The BHV-1 vaccine appeared to cause immunosuppression which interfered with response to the Pasteurella vaccine.

TABLE 6

Protection From Natural Bovine
Respiratory Disease (Vaccination Trial E)

| Group | BRD Morbidity | BRD Mortality | Fibrinous Pneumonia Mortality |
|---|---|---|---|
| I (Vaccine) | 259/1168 22.2%[a] | 6/1168 0.5%[a] | 5/1168 0.4% |
| II (Placebo) | 301/1156 26.0% | 16/1156 1.4% | 12/1156 1.0% |

[a]Significantly lower ($P < 0.05$) than Group II

EXAMPLE 2

Identification of Neutralizing Epitopes of Leukotoxin

The *P. haemolytica* leukotoxin protein contains a series of repeated amino acid domains near the carboxy terminus. These domains are likely to be epitopes useful in vaccine compositions. The consensus amino acid sequence is Gly-Gly-X-Gly-X-Asp (SEQ ID NO:4), where X is Lys, Asp, Val or Asn. (Highlander et al., *DNA* (1989) 8:15–28.) However, other substitutions likely to render immunologically active peptides include substitutions with an aliphatic amino acid, such as Gly, Ala, Val, Leu, Ile, a charged amino acid such as Asp, Glu, Arg, His or Lys, or a corresponding neutral amino acid such as Asn or Gln.

Based on this information, a synthetic peptide of the sequence GGNGDDFIDGGKGNDLLHGG (SEQ ID NO:5) was constructed by standard solid phase technology on an Applied Biosystems peptide synthesizer. Mice were immunized with authentic leukotoxins prepared from either *P. haemolytica*, or *Actinobacillus pleuropneumoniae* (serotypes 1 and 5) at 100 micrograms per dose with Freund's Complete Adjuvant (first vaccination) or Freund's Incomplete Adjuvant (all subsequent vaccinations). High titer serum samples from immunized mice were tested, in a standard ELISA, for the following: (1) their ability to react with recombinant and authentic *P. haemolytica* leukotoxin; (2) their ability to react with the toxin produced by *A. pleuropneumoniae*; and (3) their ability to react with the synthetic peptide described above. The results, summarized in Table 7, are expressed as the relative reactivity at a serum dilution of 1 in 100,000.

TABLE 7

Presence of Synthetic Peptide Epitopes in Toxins from
*P. haemolytica* and *A. pleuropneumonia* serotypes 1 and 5

| Toxin Prepared From | Relative Serological Response To: | | |
|---|---|---|---|
| | Synthetic Peptide | Actinobacillus Toxin | Pasteurella Toxin |
| *A. pleuropneumoniae* sero.5 | +++ | ++++ | ++ |
| *A. pleuropneumoniae* sero.1 | + | ++++ | + |
| *P. haemolytica* | +++ | not determined | ++++ |

This data indicated that animals vaccinated with either of the three leukotoxins developed antibodies which reacted with all toxins and a synthetic peptide based on a portion of the *P. haemolytica* toxin. Once an appropriate level of anti-peptide serum antibody was reached (ELISA titer of 100,000 or greater), spleen cells were fused with NS1 cells and monoclonal antibody-producing clones were isolated by standard techniques. Culture supernatants from these clones were tested for their ability to react with the synthetic peptide (above) and the respective toxins in an ELISA assay. The results for 2 clones are shown in Table 8.

TABLE 8

| | | Relative Reaction With: | | |
|---|---|---|---|---|
| Clone | Immunogen | Pasteurella Toxin | Synthetic Peptide | Actinobacillus Toxin |
| ET122-6A4-3 | Pasteurella toxin | ++++ | +++++ | ND[1] |
| N37-3F9-6 | Actinobacillus toxin | ND | ++++ | +++++ |

[1]Not determined

These results demonstrate that each of these monoclonal antibodies react with an epitope which is shared by the *P. haemolytica* and *A. pleuropneumoniae* toxins, and that this epitope is structurally similar to that of the synthetic peptide. This peptide is also structurally similar to a bovine rotavirus synthetic peptide of the sequence T M N G N E F Q T G G I G N L P I R N W N A C (SEQ ID NO:6), representing amino acids 40–60 of the VP6 protein. the monoclonal antibodies described above can therefore be used to determine the degree of their cross-reactivity with rotavirus proteins based on the epitope represented by the synthetic peptides. furthermore, the immunologically active leukotoxin fragments might prove useful in immunizing against rotavirus.

The antibodies above can also be tested for (1) their ability to react with and neutralize other similar toxins, including those produced by *E. coli, Proteus vulgaris, Proteus mirabilis* and *Actinobacillus actinomycetemcomitans*. A DNA sequence coding for this epitope can be cloned and expressed in either *E. coli, Staphylococcus aureus* or Baculovirus.

EXAMPLE 4

Preparation of *H. somnus* OMP Extract Enriched in Iron-Regulated Proteins 100 ml of BHITT broth containing 40% FBS was inoculated with 1 ampoule of working *H. somnus* HS25 stock produced as described above in Materials and Methods. The culture was agitated (approximately 50 rpm) at 37° C. until $O.D._{660}=0.4–0.6$. 3×1 liter flasks of BHITT containing 40% FBS were inoculated with 1.0 ml, 0.1 ml and 0.01 ml of the above culture. Flasks were incubated at 37° C. and shaking continued slowly overnight. A production fermenter containing BHITT (serum-free) was inoculated with a flask which was closest to $O.D._{660}$ of 0.5. The fermenter was run at 37° C. at an agitation rate of 250 rpm and an aeration rate of 0.5 VVM. pH was maintained at 7.2 and dissolved oxygen levels kept above 10%. When the $O.D._{660}=0.1$, dipyridyl (Sigma) was aseptically added to a final concentration of 80 $\mu$M (0.25 ml/L from a 320 mM stock solution). Growth continued until the culture entered late log phase.

Following growth, the fermenter contents were cooled to approximately 4–10° C. The culture was harvested by passing fermenter contents through a sterile ultrafiltration module equipped with 0.3 micron filter cassettes. The retentate was collected back into the fermenter or a separate, suitable sterile reservoir. Ultrafiltration continued until the fermenter contents were concentrated approximately 20 fold. The cell concentrate was diafiltered against 5–10 volumes of sterile 10 mM MOPS buffer (pH 7.4) and frozen at −70° C. for at least 24 hours. The cell concentrate was then thawed and cells passaged through a sealed, sterilized sonicator and recirculated if necessary until 95% cell disruption was achieved. Whole cells remaining were removed by passage through a sterile ultrafiltration module with 0.3 micron filter cassettes. The filtrate was retained in a sterile reservoir. Triton X-100 was added to the filtrate to a final concentration of 1% and mixed overnight at 4° C. Solubilized proteins were separated from insoluble proteins by ultrafiltration using 100,000 NMWCO membranes. The retentate was stored at −20° C. until formulation.

The product was inactivated by passage of concentrated cells through a sonicator or Dyna-Mill to achieve 95% cell disruption. Following this, the product was incubated in detergent (1% Triton x-100).

Vaccine Formulations

Prior to formulation, the material above was concentrated by centrifugation to a protein concentration of approximately 2.5 mg/ml. The product was standardized to contain 100 μg/2 ml dose (110 μg±10 μg) as determined by a standard ELISA assay. Emulsigen Plus (MVP Laboratories, Ralston, Nebr.) was used as adjuvant at 30% of the total volume being adjuvanated. Thimerasol was used as a preservative at a concentration of 0.01% W/V. A 40 L serial was made which had the following proportions:

12.0 L Emulsigen Plus;
0.8 L Protein Antigen (concentrated at 2.5 mg/ml); and
27.2 L 0.85% saline.

The vaccine was stored at 2°–7° C. (35°–45° F.).

EXAMPLE 5

Protective Capacity of the *H. somnus* OMP Extract Enriched with Iron Regulated Proteins The ability of the *H. somnus* OMP extract from Example 4 to protect calves against experimentally induced *H. somnus* disease was tested as follows. Three groups of six calves each were vaccinated intramuscularly twice, 21 days apart, with the *H. somnus* OMP vaccine formulation (2 ml/dose, 100 μg protein/dose), a commercial *H. somnus* bacterin (Somnugen, Boehringer Ingelheim Animal Health Inc., used as directed by the manufacturer), or a placebo (Emulsigen Plus in saline, 2 ml/dose). The calves were four- to six-month-old beef-type animals purchased from a commercial cow-calf herd.

Ten days after the second vaccination, the calves were challenged by intravenous injection of $10^8$ colony-forming units of virulent *H. somnus* strain HS-25. In unvaccinated calves, this challenge results in the occurrence of disease characterized by bacteremia, depression, lameness, myocarditis, pneumonia, and arthritis similar to that reported in field cases of the disease.

To determine efficacy, all calves were examined daily by a veterinarian for clinical signs of illness for 14 days following challenge with *H. somnus*. Blood samples were collected daily by aseptic technique from the right jugular vein and were cultured for the presence of *H. somnus* organisms. Bacteremia is thought to be an important early step in the pathogenesis of the *H. somnus* disease complex. By preventing this phase, other clinical manifestations of the disease which occur under field conditions are significantly reduced. A post mortem examination was conducted by a veterinarian on all calves that died. Antibody titers to *H. somnus* were measured using an ELISA at the time of the first vaccination and on the day of challenge.

None of the calves in this trial died. However, four of six calves in the control group developed signs of *H. somnus* infection.

TABLE 9

| | Clinical Response Following Challenge (6 calves per group) | | | | |
|---|---|---|---|---|---|
| | Bacteremia | % Morbidity[a] | Lameness | Depression | Antibody Titer[b] |
| 1. Placebo | 4 | 3 | 3 | 1 | 5.1 |
| 2. *H. somnus* Bacterin | 3 | 3 | 3 | 2 | 1.7 |
| 3. *H. somnus* OMP extract | 0* | 1 | 1 | 0 | 19.7* |

[a]Number of calves that developed a fever >40.0° C. with clinical signs of *H. somnus* infection.
[b]Ratio of *H. somnus* antibody titer (ELISA) at challenge/day 0.
*Significantly lower or higher ($p < 0.05$) than the control group. Fisher's Exact Test.

This experimental challenge model reproduces localized infection and lesions at body sites which are typical of field cases of *H. somnus* infection. However, this requires intravenous injection of a large number of virulent bacteria which probably does not occur under field conditions. In the face of such a large challenge, prevention of bacteremia is an indicator of protection. The subsequent occurrence of localized infection, even in vaccinated calves, is probably due to the severe challenge.

As can be seen in Table 9, the *H. somnus* OMP extract enriched in iron-regulated proteins prevented bacteremia and depression and reduced morbidity and lameness as compared to the control group. The commercial bacterin did not significantly reduce the level of disease as compared to the control group. Additional data on the efficacy of the *H. somnus* bacterial extract are provided below in Example 6.

Most effective protection was seen when calves were vaccinated two times, two to six weeks apart. For calves destined for a feedlot, the greatest benefit is obtained by administering the first dose two to six weeks prior to feedlot entry and the second does at the time of arrival at the feedlot. Animals vaccinated prior to six months of age may require a booster after six months of age. Furthermore, annual re-vaccination of mature animals may be desirable.

The safety of the *H. somnus* OMP extract was tested in field trials. Over 7,000 calves were vaccinated either once or twice with the *H. somnus* OMP extract. No local or systemic adverse reactions were reported. Under experimental conditions, no adverse reactions occurred in calves vaccinated with ten times the normal dose.

EXAMPLE 6

Protective Capacity of the *H. somnus* OMP Extract Combined with *P. haemolytica* Antigens In this example, the OMP extract, produced as described in Example 4, was combined with recombinantly produced LKT 352 (as described in Example 1) and a saline extract of *P. haemolytica* (produced as described in Example 1 for Vaccination Trial A) to yield a "combination vaccine." To test the efficacy of the combination vaccine, three groups of calves were vaccinated intramuscularly as follows: Group 1, placebo control (Emulsigen Plus in saline, 2 ml/dose); Group 2, one dose of the combination vaccine (made by combining 0.56 ml of the *H. somnus* OMP extract to the LKT 352/saline extract vaccine described in Example 1 for Vaccination Trial D), 31 days before challenge; Group 3, two doses of the combination vaccine 31 and 10 days before challenge. Calves were yearling beef-type animals purchased from a commercial cow-calf herd.

31 days after the first vaccination, the calves were challenged with an intravenous inoculation of $10^8$ colony-forming units of virulent *H. somnus* strain HS-25. In unvaccinated calves, this challenge induces bacteremia followed by variable signs of the *H. somnus* disease complex.

To determine efficacy, calves were examined by a veterinarian for clinical signs of illness for 14 days following challenge with *H. somnus*. Blood samples were collected daily by aseptic technique from the right jugular vein and were cultured for the presence of *H. somnus* organisms. A post mortem examination was conducted by a veterinarian on all calves. Antibody titers to *H. somnus* were measured using an ELISA at the time of the first vaccination and on the day of challenge.

chute. After arrival at the feedlot, the calves were housed together in one pen adjacent to approximately 4,500 cattle in surrounding pens. Feedlot staff were not aware of the vaccination status of each calf and identified and treated sick animals using their standard procedures.

TABLE 11

| Vaccine | Treatment Rate |
|---|---|
| Combination Vaccine | 1/45 2%* |
| Commercial Bacterin | 12/41 29% |

*Significantly lower ($p < 0.001$) than the group given the commercial bacterin.

As can be seen in table 11, two doses of the combination vaccine were highly effective at preventing natural feedlot disease when the first dose was given two weeks before feedlot arrival.

In order to test the protective capacity of the combination vaccine in ranch calves retained at the ranch for feeding the following experiment was conducted. A group of 88 heifer calves (5–6 months of age) was divided into two groups and vaccinated twice. The first vaccination was administered two weeks before weaning and the second dose was given at weaning. Two vaccines were used:

1. Combination vaccine (2 ml/dose), 45 calves;
2. Commercial *H. somnus* bacterin (Somnugen, Boehringer Ingelheim Animal Health Inc., used as directed by the manufacturer), 43 calves.

TABLE 10

Clinical Response Following Challenge (6 calves per group)

| | Bacteremia | Morbidity[a] | Lameness | Depression | Average PM Lesions[b] | ELISA TITER Increase[c] |
|---|---|---|---|---|---|---|
| 1. Placebo | 5 | 6 | 5 | 2 | 2.6 | 1.78 |
| 2. Combination Vaccine, 1 vaccination | 4 | 5 | 3 | 1 | 3.0 | 4.33 |
| 3. Combination Vaccine, 2 vaccinations | 0* | 6 | 6 | 1 | 0.9 | 16.50* |

[a]% of calves that developed a fever > 40.0° C. and clinical signs of *H. somnus* infection.
[b]Lesions found at post mortem examination 14 days after challenge. Lesions in the heart, pleura, joints, tendons, kidneys, and muscle were scored from 0 (no lesion) to 3 (severe lesions), and the scores for each calf were used to calculate the group mean.
[c]Ratio of *H. somnus* antibody titer (ELISA) on day 31/day 0.
*Significantly lower or higher ($p < 0.05$) than the control group. Fisher's Exact Test.

As can be seen in Table 10, two doses of the combination vaccine prevented bacteremia and reduced the degree of infection at local sites. However, a single dose given to previously unvaccinated calves did not protect against experimental challenge.

Field trials were also conducted to test the protective capacity of the combination vaccine in ranch calves destined for a commercial feedlot. A group of 86 steer calves (5–6 months of age) was divided into two groups. All calves were vaccinated twice at two weeks before weaning and again at the time of weaning and trucking to a commercial feedlot. Two vaccines were used:

1. The combination vaccine (2 ml/dose), 45 calves;
2. A commercial *H. somnus* bacterin (Somnugen, Boehringer Ingelheim Animal Health Inc., used as directed by the manufacturer), 41 calves.

Animals were assigned to each treatment group without bias, alternating between groups as they passed through the Animals were assigned without treatment bias, alternating between groups according to chute order. After weaning, calves were housed together in one pen on the ranch. Sick animals were identified and treated by ranch staff using standard procedures. The treatment rates are summarized in Table 12 below.

TABLE 12

| Vaccine | Treatment Rate |
|---|---|
| Combination Vaccine | 0/45 0%* |
| Commercial Bacterin | 11/43 26% |

*Significantly lower ($p < 0.001$) than the group given the commercial bacterin.

As can be seen, two doses of the combination vaccine were highly effective in preventing natural disease in ranch-fed calves when the first dose was given two weeks prior to weaning.

To test the safety of the vaccine, over 15,000 calves were vaccinated with the combination vaccine without any detectable adverse local or systemic reactions. In addition, calves were vaccinated with ten times the normal dose under experimental conditions and did not experience any adverse reactions.

Thus, the combined vaccine formulation stimulates a humoral immune response against *H. somnus* and agglutinating plus anti-leukotoxin antibodies against *P. haemolytica*. The vaccine is efficacious and safe. Best results are obtained when calves are vaccinated two times, two to six weeks apart. For calves destined for a feedlot, the greatest benefit is obtained by administering the first dose two to six weeks prior to feedlot entry and the second does at the time of arrival at the feedlot. Animals vaccinated prior to six months of age may require a booster after six months of age. Furthermore, annual revaccination of mature animals may be desirable.

Thus, *H. somnus* OMP vaccines enriched in iron-regulated proteins are disclosed. Although preferred embodiments of the subject invention have been described in some detail, it is understood that obvious variations can be made without departing from the spirit and the scope of the invention as defined by the appended claims.

We claim:

1. A vaccine composition comprising a pharmaceutically acceptable vehicle, an adjuvant, and an outer membrane protein extract comprising a mixture of *Haemophilus somnus* proteins, wherein said extract is enriched with iron-regulated proteins, and further wherein the vaccine composition is produced by a method comprising:

(a) culturing *H. somnus* cells under iron-restricted conditions;

(b) disrupting the *H. somnus* cells cultured as in step (a);

(c) extracting cell membranes to render an *H. somnus* outer membrane protein extract enriched in iron-regulated proteins; and (d) combining said *H. somnus* outer membrane protein extract with a pharmaceutically acceptable vehicle and an adjuvant.

2. A method of treating or preventing *Haemophilus somnus* infection in a vertebrate subject comprising administering to said subject a therapeutically effective amount of a vaccine composition according to claim 1.

3. The composition of claim 1, wherein the *H. somnus* cells are cultured in the presence of a chelating agent which scavenges iron.

4. The composition of claim 3, wherein the chelating agent is dipyridyl.

5. The composition of claim 1, wherein cell membranes are extracted using a detergent.

6. A vaccine composition comprising a pharmaceutically acceptable vehicle, an adjuvant, and an outer membrane protein extract comprising a mixture of *Haemophilus somnus* proteins, wherein said extract is enriched with iron-regulated proteins, and further wherein the vaccine composition is produced by a method comprising:

(a) culturing *H. somnus* cells;

(b) adding an iron-scavenging agent to the *H. somnus* cell culture during mid-log phase;

(c) disrupting the *H. somnus* cells cultured as in step (b) during late-log phase;

(d) extracting cell membranes using detergent to render an *H. somnus* outer membrane protein extract enriched in iron-regulated proteins; and (e) combining said *H. somnus* outer membrane protein extract with a pharmaceutically acceptable vehicle and an adjuvant.

7. The composition of claim 6, wherein the iron-scavenging agent is dipyridyl.

8. A method of treating or preventing *Haemophilus somnus* infection in a vertebrate subject comprising administering to said subject a therapeutically effective amount of a vaccine composition according to claim 6.

* * * * *